United States Patent
Raby et al.

(10) Patent No.: US 11,058,516 B2
(45) Date of Patent: Jul. 13, 2021

(54) ORTHODONTIC PALATAL EXPANDER INCLUDING SPLIT BEAMS

(71) Applicant: 3M INNOVATIVE PROPERTIES COMPANY, St. Paul, MN (US)

(72) Inventors: Richard E. Raby, Lino Lakes, MN (US); Chaodi Li, Woodbury, MN (US); Fay T. Salmon, Eden Prairie, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/753,446

(22) PCT Filed: Sep. 18, 2018

(86) PCT No.: PCT/IB2018/057169
§ 371 (c)(1),
(2) Date: Apr. 3, 2020

(87) PCT Pub. No.: WO2019/069163
PCT Pub. Date: Apr. 11, 2019

(65) Prior Publication Data
US 2020/0253696 A1 Aug. 13, 2020

Related U.S. Application Data

(60) Provisional application No. 62/568,913, filed on Oct. 6, 2017.

(51) Int. Cl.
*A61C 7/10* (2006.01)
*G16H 50/50* (2018.01)
(Continued)

(52) U.S. Cl.
CPC ............... *A61C 7/10* (2013.01); *A61C 7/002* (2013.01); *A61C 7/08* (2013.01); *G06F 30/10* (2020.01);
(Continued)

(58) Field of Classification Search
CPC .............. A61C 7/10; A61C 7/002; A61C 7/08
See application file for complete search history.

(56) References Cited

U.S. PATENT DOCUMENTS 5,312,247 A * 5/1994 Sachdeva ................. A61C 7/10
433/18
5,376,001 A * 12/1994 Tepper ..................... A61C 7/00
433/6
(Continued)

FOREIGN PATENT DOCUMENTS

CN 204839789 U 12/2015
EP 2 311 402 A1 4/2011
(Continued)

OTHER PUBLICATIONS

International Search Report for PCT International Application No. PCT/IB2018/057169, dated Jan. 18, 2019, 8 pages.

*Primary Examiner* — Ralph A Lewis
(74) *Attorney, Agent, or Firm* — Kevin Weber

(57) ABSTRACT

An orthodontic palatal expander may include a first shell configured to receive at least one tooth of a first posterior segment of a dental arch of a patient; a second shell configured to receive at least one tooth of a second posterior segment of the dental arch; and a split beam connected between the first shell and the second shell. The split beam may include a first beam comprising a relatively high modulus material, a second beam comprising the high modulus material, and a region between the first beam and the second beam.

20 Claims, 9 Drawing Sheets

(51) Int. Cl.
*G06F 30/10* (2020.01)
*A61C 7/00* (2006.01)
*A61C 7/08* (2006.01)
*G06F 111/04* (2020.01)

(52) U.S. Cl.
CPC .......... *G16H 50/50* (2018.01); *G06F 2111/04* (2020.01)

(56) References Cited

U.S. PATENT DOCUMENTS

| | | | |
|---|---|---|---|
| 6,450,806 B2* | 9/2002 | Winsauer | A61C 7/10 433/7 |
| 6,572,372 B1 | 6/2003 | Phan | |
| 6,845,175 B2 | 1/2005 | Kopelman | |
| 7,011,518 B2* | 3/2006 | DeLuke | A61C 7/10 433/7 |
| 7,027,642 B2 | 4/2006 | Rubbert | |
| 7,234,937 B2 | 6/2007 | Sachdeva | |
| 7,357,633 B2* | 4/2008 | Mailyan | A61C 7/10 433/7 |
| 7,731,495 B2 | 6/2010 | Eisenberg | |
| 8,192,196 B2* | 6/2012 | Singh | A61F 5/566 433/7 |
| 8,194,067 B2 | 6/2012 | Raby | |
| 8,491,306 B2 | 7/2013 | Raby | |
| 8,651,857 B2 | 2/2014 | Geenty | |
| 8,738,165 B2 | 5/2014 | Cinader, Jr. | |
| 9,345,557 B2 | 5/2016 | Anderson | |
| 9,351,810 B2* | 5/2016 | Moon | A61C 7/10 |
| 9,532,854 B2 | 1/2017 | Cinader, Jr. | |
| 10,449,016 B2* | 10/2019 | Kimura | A61C 7/08 |
| 2004/0009449 A1 | 1/2004 | Mah | |
| 2004/0029068 A1 | 2/2004 | Sachdeva | |
| 2005/0186524 A1* | 8/2005 | Abolfathi | A61C 7/10 433/7 |
| 2006/0093983 A1 | 5/2006 | Schultz | |
| 2007/0031791 A1 | 2/2007 | Cinader, Jr. | |
| 2007/0065768 A1* | 3/2007 | Nadav | |
| 2008/0020337 A1 | 1/2008 | Phan | |
| 2009/0098500 A1 | 4/2009 | Diaz Rendon | |
| 2009/0148803 A1 | 6/2009 | Kuo | |
| 2013/0325431 A1 | 12/2013 | See | |
| 2014/0363779 A1 | 12/2014 | Kopelman | |
| 2015/0140501 A1 | 5/2015 | Kim | |
| 2015/0157421 A1 | 6/2015 | Martz | |
| 2015/0216627 A1 | 8/2015 | Kopelman | |
| 2016/0067014 A1 | 3/2016 | Kottemann | |
| 2016/0193014 A1 | 7/2016 | Morton | |
| 2016/0310236 A1 | 10/2016 | Kopelman | |
| 2017/0007366 A1* | 1/2017 | Kopelman | G06Q 30/0643 |
| 2017/0065373 A1 | 3/2017 | Martz | |
| 2017/0079747 A1* | 3/2017 | Graf | A61C 7/002 |
| 2017/0304108 A1* | 10/2017 | Simonetti | A61F 5/566 |

FOREIGN PATENT DOCUMENTS

| | | |
|---|---|---|
| JP | 2003038520 | 2/2003 |
| JP | 2011517603 | 6/2011 |
| JP | 2011212132 | 10/2011 |
| KR | 1020100109898 | 10/2010 |
| KR | 200465679 | 3/2013 |
| KR | 1020150119597 | 10/2015 |
| KR | 1020170071155 | 6/2017 |
| KR | 1020170102471 | 9/2017 |
| WO | WO 2006-096558 | 9/2006 |
| WO | WO 2007-084727 | 7/2007 |
| WO | WO 2014-128423 | 8/2014 |
| WO | WO 2015-114450 | 8/2015 |
| WO | WO 2015-140614 | 9/2015 |
| WO | WO 2019-023166 | 1/2019 |
| WO | WO 2019-069162 | 4/2019 |
| WO | WO 2019-069164 | 4/2019 |
| WO | WO 2019-069165 | 4/2019 |
| WO | WO 2019-069166 | 4/2019 |
| WO | WO 2019-069268 | 4/2019 |

* cited by examiner

```
162 → Receive digital representation of 3D dental anatomy of a patient
164 → Determine dimensions and shapes of a set of palatal expanders
166 → Present representations of the set of palatal expanders to a user
168 → Send digital model of set of palatal expanders to automated manufacturing system
170 → Manufacture set of palatal expanders
```

ORTHODONTIC PALATAL EXPANDER INCLUDING SPLIT BEAMS

CROSS REFERENCE TO RELATED APPLICATIONS

This application is a national stage filing under 35 U.S.C. 371 of PCT/IB2018/057170, filed Sep. 18, 2018, which claims the benefit of provisional Application No. 62/568,913, filed Oct. 6, 2017, the disclosure of which is incorporated by reference in its/their entirety herein.

TECHNICAL FIELD

This disclosure relates to orthodontic palatal expanders.

BACKGROUND

The field of orthodontics relates to repositioning a patient's teeth for improved function and aesthetic appearance. Orthodontic devices and treatment methods generally involve the application of forces to move teeth into a proper bite configuration, or occlusion. As one example, orthodontic treatment may involve the use of slotted appliances, known as brackets, which are fixed to the patient's anterior, cuspid, and bicuspid teeth. An archwire is typically placed in the slot of each bracket and serves as a track to guide movement of the teeth to desired orientations. The ends of the archwire are usually received in appliances known as buccal tubes that are secured to the patient's molar teeth. Such dental appliances remain in the mouth of the patient and are periodically adjusted by an orthodontist to check the process and maintain the proper force levels on the teeth until proper dental alignment is achieved.

In orthodontic cases where the width of the maxillary dental arch is abnormally small (i.e. narrow) relative to the mandibular arch, palatal expansion may be prescribed. Such cases often exhibit dental cross-bites where one or both posterior segments of teeth in the maxilla are laterally displaced by as much as a full cusp, resulting in poor, if not completely incorrect, intercuspation of the teeth. In such cases, an orthodontic palatal expander may be installed within the patient's mouth to gently expand the roof of the mouth and upper jaw of the patient over time. A conventional appliance may consist of stainless steel bands cemented to the molars and bicuspids and soldered to heavy gauge stainless steel wires, which are in turn soldered to a turnbuckle mechanism that can be periodically adjusted to expand the palate. Additional bracing wires may be incorporated into the appliance to give support to neighboring teeth.

SUMMARY

In general, the disclosure describes various orthodontic palatal expanders having split-beams that cause natural expansion in a horizontal plane as the beams relax from initial deflected states. Various examples are described, including one-piece orthodontic palatal expanders suited for additive manufacturing techniques, such as 3D printing, thereby avoiding manual fabrication or assembly of components.

In some examples, the disclosure describes an orthodontic palatal expander including a first shell configured to receive at least one tooth of a first posterior segment of a dental arch of a patient; a second shell configured to receive at least one tooth of a second posterior segment of the dental arch; and a split beam connected between the first shell and the second shell. The split beam includes a first beam comprising a relatively high modulus material, a second beam comprising the high modulus material, and a region between the first beam and the second beam.

In some examples, the disclosure describes a system including an ordered set of orthodontic palatal expanders configured to expand a palate of a patient. Each orthodontic palatal expander in the ordered set of orthodontic palatal expanders includes a first shell configured to receive at least one tooth of a first posterior segment of a dental arch of a patient; a second shell configured to receive at least one tooth of a second posterior segment of the dental arch; and a split beam connected between the first shell and the second shell. The split beam includes a first beam comprising a relatively high modulus material, a second beam comprising the high modulus material, and a region between the first beam and the second beam.

In some examples, the disclosure describes a method including forming a model of dental anatomy of a patient; and forming, based on the model, an orthodontic palatal expander. The orthodontic palatal expander includes a first shell configured to receive at least one tooth of a first posterior segment of a dental arch of a patient; a second shell configured to receive at least one tooth of a second posterior segment of the dental arch; and a split beam connected between the first shell and the second shell. The split beam includes a first beam comprising a relatively high modulus material, a second beam comprising the high modulus material, and a region between the first beam and the second beam.

In some examples, the disclosure describes a method including receiving, by a computing device, a digital representation of a three-dimensional (3D) dental anatomy of a patient, the dental anatomy providing initial positions of one or more teeth of the patient. The method also includes determining, by the computing device, dimensions and shapes of an orthodontic palatal expander for the patient. The dimensions and shapes of the removable dental appliance are configured to reposition the one or more teeth of the patient from their initial positions to adjusted positions when the orthodontic palatal expander is worn by the patient. The dimensions and shapes of the orthodontic palatal expander include a position, dimension and shape of a first shell configured to receive at least one tooth of a first posterior segment of a dental arch; a position, dimension, and shape of a second shell configured to receive at least one tooth of a second posterior segment of the dental arch; and a position, dimension, and shape of a split beam connected between the first shell and the second shell. The split beam comprises a first beam comprising a relatively high modulus material, a second beam comprising the high modulus material, and a region between the first beam and the second beam. The method also includes transmitting, by the computing device, a representation of the orthodontic palatal expander to a computer-aided manufacturing system.

In some examples, the disclosure describes a non-transitory computer-readable storage medium that stores computer system-executable instructions that, when executed, configure a processor to perform any of the methods described herein.

The details of one or more examples of this disclosure are set forth in the accompanying drawings and the description below. Other features, objects, and advantages of this disclosure will be apparent from the description and drawings, and from the claims.

DETAILED DESCRIPTION

Figure 1A:
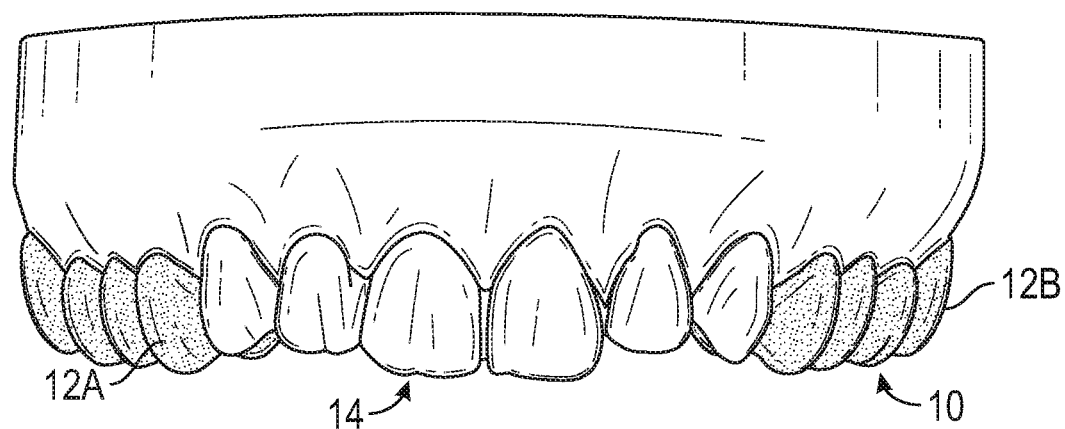
FIG. 1A is a facial view of an example orthodontic palatal expander including split beams installed on a dental arch of a patient.

This disclosure describes orthodontic palatal expanders that include at least one split beam attached between a first shell and a second shell. The first shell is configured to receive at least one tooth of a first posterior segment of a dental arch of a patient, and the second shell is configured to receive at least one tooth of a second posterior segment of the dental arch of the patient. The at least one split beam may include a first beam including a relatively high modulus material, a second beam including the high modulus material, and a region between the first beam and the second beam. The region between the first beam and the second beam may be at least partially filled with a relatively low modulus, elastomeric material, or may be left substantially fully open.

The at least one split beam may be similar to a laminated beam or I-beam that includes parallel flanges and a shear web, but may omit the shear web or form the shear web with a relatively low modulus, elastomeric material. This construction may allow for a relatively large amount of deflection of the at least one split beams while allowing control of the magnitude and direction of rotation at the ends of the first and second beams, e.g., by controlling relative lengths of the first and second beams, attachment points of the respective ends of the first and second beams to other structures, such as the first and second shells, or the like. For example, by forming the first and second beams to have respective lengths and attachment points so that the first and second beams and the surfaces to which the first and second beams attach define a parallelogram, the first and second shells will expand in a horizontal plane as the beams exert forces on the first and second shells, which may cause or allow rotation of the first and second shells and, ultimately, the teeth received by the first and second shells. On the other hand, by forming the first and second beams to have respective lengths and attachment points so that the first and second beams and the surfaces to which the first and second beams attach define a trapezoid, the ends of the first and second beams may rotate in opposite directions as the beams exert forces on the first and second shells, which may counteract reaction torque of teeth received by the first and second shells due to displaced centers of rotation of the at least one teeth of the first posterior segment and at least one teeth of the second posterior segment. In this way, the split beam may enable control over rotation of the at least one teeth of the first posterior segment and at least one teeth of the second posterior segment.

Orthodontic palatal expanders may be used in patients in which a width of a maxillary dental arch of the patient is abnormally narrow relative to a width of the mandibular arch. Such patients may exhibit dental cross-bites where one or both posterior segments of teeth in the maxilla are laterally displaced by as much as a full cusp, resulting in poor, if not completely incorrect, intercuspation of the teeth. Expansion is indicated in somewhere between 8% and 18% of orthodontic patients and is usually part of a Phase I treatment, meaning it is performed as a course of treatment prior to conventional braces being applied. Although, in some cases, braces or other tooth-moving devices may be used in conjunction with palatal expansion to correct anterior tooth positions during expansion.

In some examples, expansion can occur at a rate of about 1 to 2 mm per week without causing the patient excessive discomfort. Using a conventional expander, such as a Rapid Palatal Expander (RPE), the patient, or the patient's parent, inserts a key into a hole in the middle of a turnbuckle screw and rotates it, usually a quarter-turn, to advance the screw. Because the screw has oppositely pitched threads on either side of the mid-section, this drives the nuts of the turnbuckle apart in a horizontal direction, along the axis of the screw.

Depending on the amount of expansion needed, the RPE appliance may be activated for anywhere from 2 weeks to several weeks. After the active expansion period ends, the RPE appliance is kept in place for about 3 months to allow for ossification of new bone in the gap of the mid-palatal suture. This period is needed to give stability to the maxilla before the RPE appliance can be removed and the next phase of orthodontic treatment can begin. Premature removal of the appliance is likely to result in relapse, or closure of the mid-palatal suture. This is caused by fibrous tissues in the suture that are still under tension, which can pull the plates of the maxilla back together if unobstructed by new bone deposits. As ossification occurs, these tissues remodel, and tension is relieved.

In some cases, slow palatal expansion may be used. This approach is similar to rapid palatal expansion, except that lower forces are used, and the rate of expansion (about 0.5 mm to about 1.0 mm per week) is little more than the rate at which bone can ossify to fill the expanding gap in the mid-palatal suture. As a result, the gap is never much wider than normal, because more time is given for new bone to deposit in place of the soft tissues under tension. This tends to produce a more stable occlusion with less propensity for relapse. Modern examples of slow palatal expanders usually include pre-bent nickel-titanium (NiTi) wires to achieve a relatively constant force delivery over a large deflection range.

The orthodontic palatal expanders described herein may be similar to slow palatal expanders in that the palatal expanders described herein include spring elements that apply force with a relatively continuous duty cycle. However, the orthodontic palatal expanders described herein include at least one split beam, which enables control over rotational forces applied to the teeth of the posterior segments to which the orthodontic palatal expander is coupled.

In some examples, the orthodontic palatal expanders described herein may include a connecting plate. The connecting plate may be between the first shell and the second shell, and may be configured to be positioned adjacent to a palate of the patient or a lingual surface of an anterior segment of the dental arch of the patient. At least a first split beam may be connected between the connecting plate and the first shell, and at least a second split beam may be connected between the connecting plate and the second shell. In other examples, the orthodontic palatal expanders may omit a connecting plate, and the split beams may be directly connected between the first shell and the second shell.

Figure 1B:
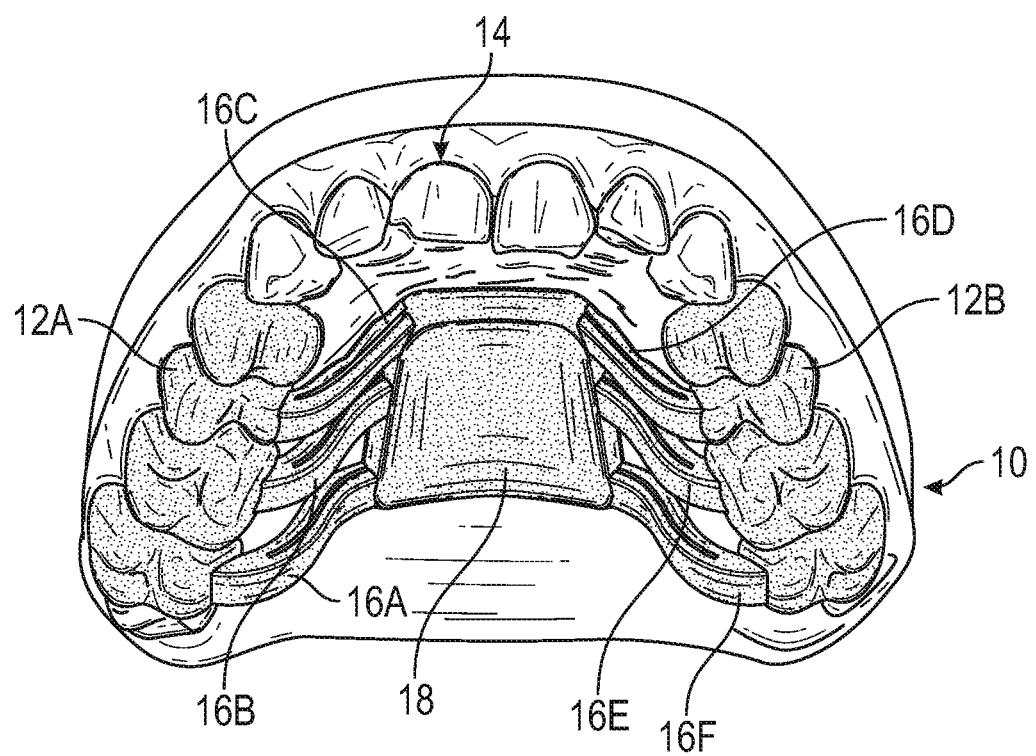
FIG. 1B is a facial-occlusal view of the example orthodontic palatal expander of FIG. 1A installed on a dental arch of a patient.
Figure 1C:
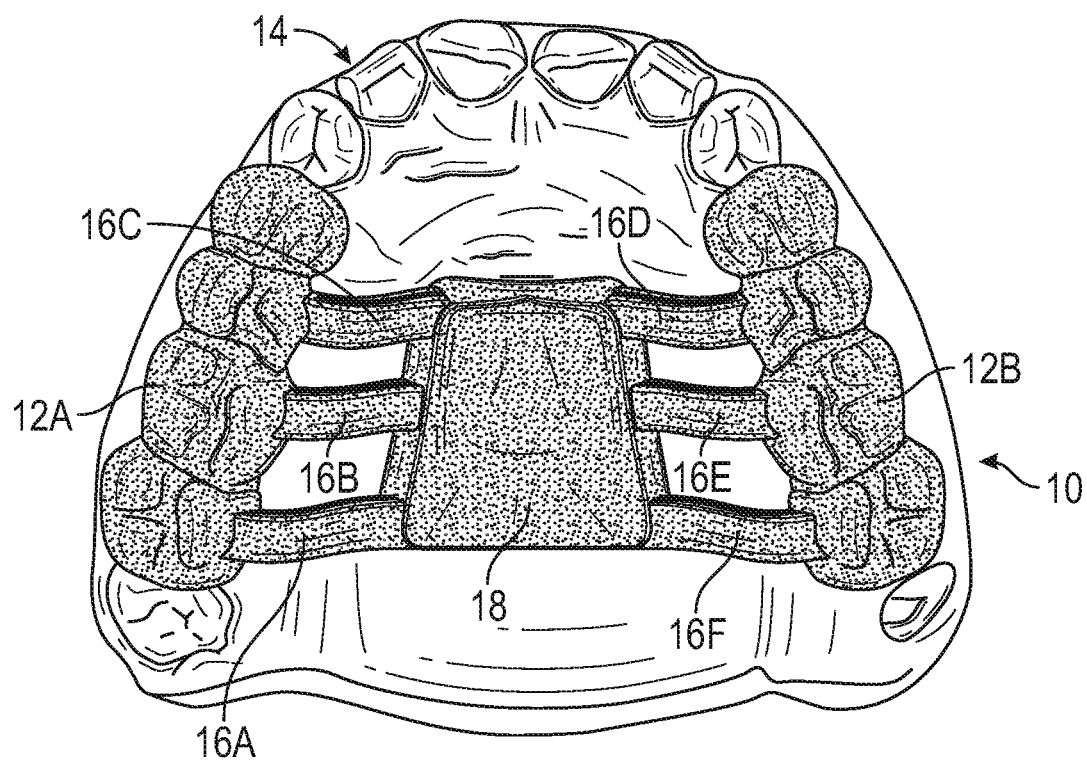
FIG. 1C is an occlusal view of the example orthodontic palatal expander of FIG. 1A installed on a dental arch of a patient.
Figure 1D:
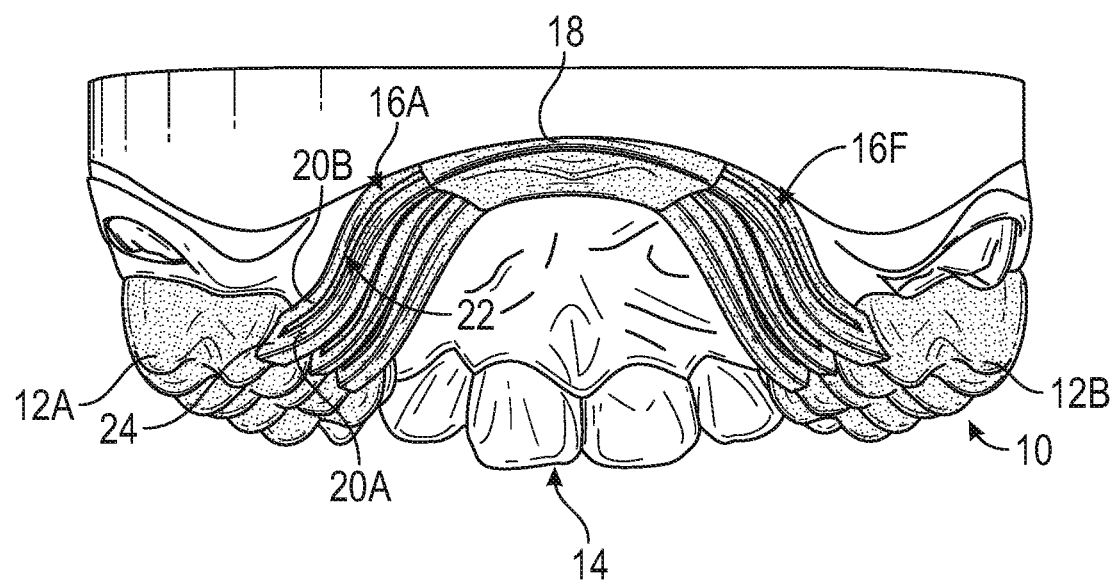
FIG. 1D is a lingual view of the example orthodontic palatal expander of FIG. 1A installed on a dental arch of a patient.
Figure 1E:
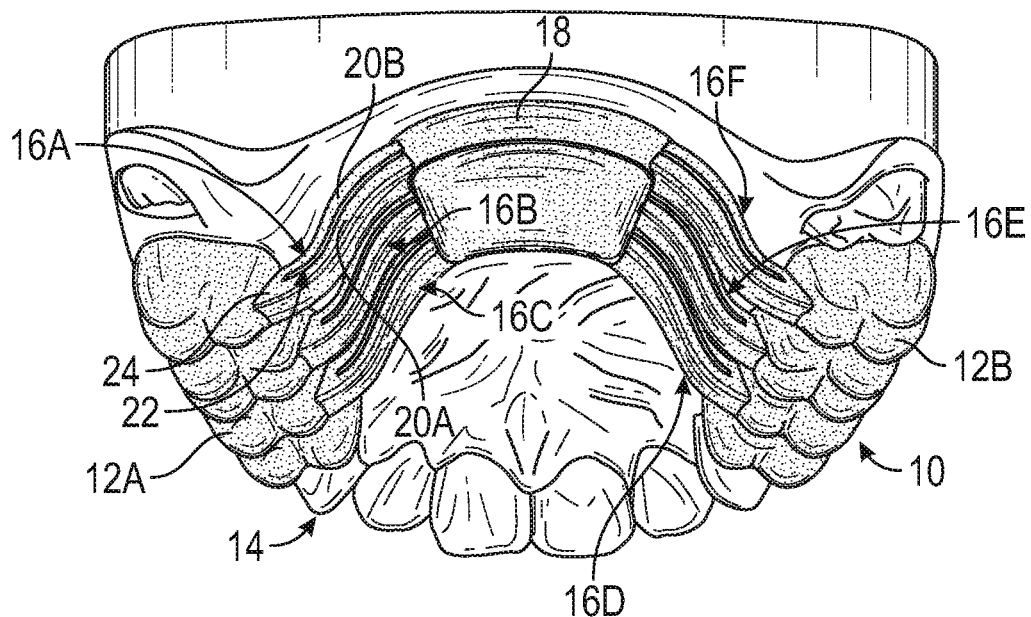
FIG. 1E is a lingual-occlusal view of the example orthodontic palatal expander of FIG. 1A installed on a dental arch of a patient.
Figure 1F:
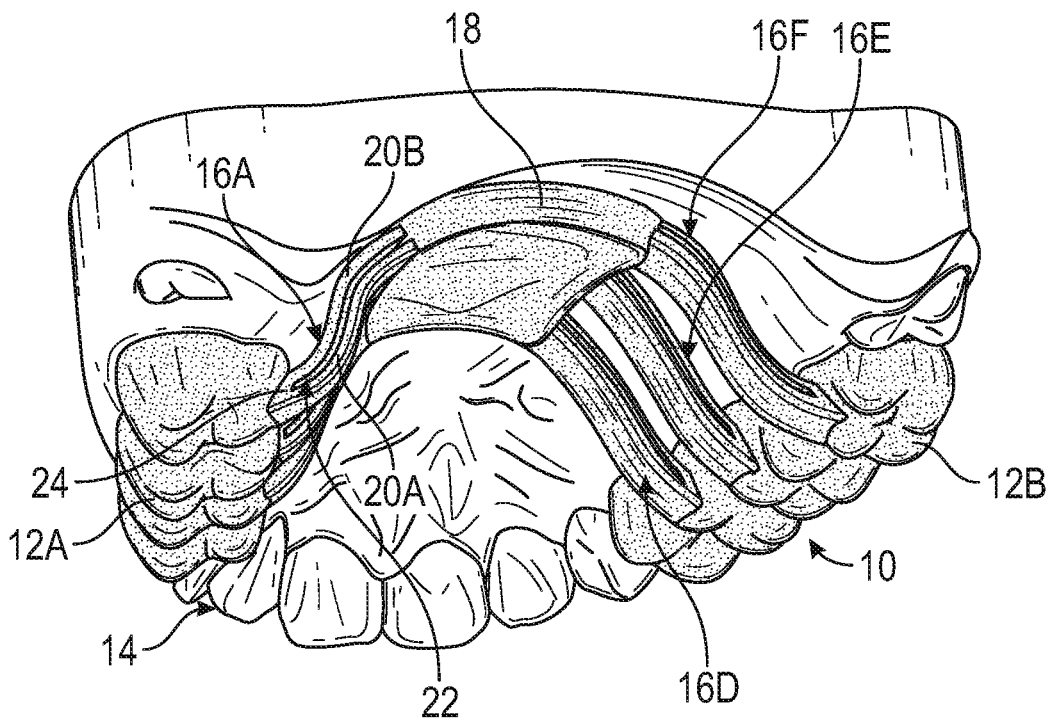
FIG. 1F is an oblique lingual view of the example orthodontic palatal expander of FIG. 1A installed on a dental arch of a patient.

FIGS. 1A-1F illustrate various views of an example orthodontic palatal expander 10 that includes a first shell 12A, a second shell 12B, and at least one split beam (e.g., split beams 16A-16F (collectively, "split beams 16")). FIG. 1A is a facial view of orthodontic palatal expander 10 including split beams 16 installed on a dental arch of a patient. FIG. 1B is a facial-occlusal view of orthodontic palatal expander 10 installed on a dental arch of a patient. FIG. 1C is an occlusal view of orthodontic palatal expander 10 installed on a dental arch of a patient. FIG. 1D is a lingual view of orthodontic palatal expander 10 installed on a dental arch of a patient. FIG. 1E is a lingual-occlusal view of orthodontic palatal expander 10 installed on a dental arch of a patient. FIG. 1F is an oblique lingual view of orthodontic palatal expander 10 installed on a dental arch of a patient.

Orthodontic palatal expander 10 includes first shell 12A and second shell 12B (collectively, "shells 12"). First shell 12A is configured to receive at least one tooth of a first posterior segment of a dental arch. For example, the dental arch may be the maxillary arch. The at least one tooth may include all or less than all posterior teeth of the first posterior segment. First shell 12A includes a wall that is shaped and defines cavities shaped to receive the at least one tooth.

Similarly, second shell 12B is configured to receive at least one tooth of a second posterior segment of the same dental arch. The at least one tooth may include all or less than all posterior teeth of the second posterior segment. In some examples, the number of teeth of the first posterior segment is the same as the number of teeth of the second posterior segment. Second shell 12B includes a wall that is shaped and defines cavities shaped to receive the at least one tooth.

In some examples, shells 12 include walls that are shaped and define cavities shaped to correspond to the initial positions of the at least one tooth in each of shells 12. In these examples, first shell 12A may not cause relative movement between teeth received in first shell 12A, and second shell 12B may not cause relative movement between teeth received in second shell 12B. Rather, shells 12 may provide anchoring points for forces to be applied to the respective at least one tooth to enable expansion of the palate of the patient.

In other examples, shells 12 include walls that are shaped and define cavities shaped to correspond to a desired position of the at least one tooth in each of shells 12. The desired position may correspond to an intermediate or a final position desired for the at least one tooth in each of shells 12. In these examples, shells 12 may both provide anchoring points for forces to be applied to the respective at least one tooth to enable expansion of the palate of the patient and be alignment trays that reposition teeth in the respective shells 12 relative to each other.

Shells 12 may be formed from a single polymer, or substantially homogeneous mixture of one or more polymers. The polymers may include biocompatible polymers, such as biocompatible thermoplastic polymers. For example, each of shells 12 may consist of a single, continuous 3D printed component. As other examples, each of shells 12 may be thermoformed from a thermoplastic sheet or molded or sculpted from an acrylic polymer resin. Each of shells 12 may optionally include chamfers or fillets on edges of shells 12 and other spaces. Such chamfers or fillets may improve patient comfort and reduce the visibility of shells 12.

In some examples, shells 12 may include one or more additional materials (in addition to polymers). For example, shells 12 may include one or more metallic components configured to provide greater durability to portions of shells 12. For instance, occlusal surfaces of shells 12 may include metal occlusal components, which may provide greater durability to resist the stress of high-pressure occlusal contact, such as bruxing, mastication, or the like.

The walls of shells 12 may define a thickness sufficient to withstand the forces applied by the remaining components of orthodontic palatal expander 10, such as split beams 16. For example, the walls of shells 12 may define a thickness of between about 0.2 mm and about 5 mm, such as between about 0.5 mm and about 3 mm, or between about 0.5 mm and about 2 mm, or about 1 mm. In some examples, thinner walls may be reinforced with metal or fabricated of metal. In some examples in which the walls of shells 12 define a larger thickness, occlusal walls of shells 12 may be relatively thinner than lingual and buccal walls of shells 12 to allow the patient to close their bite more fully.

Orthodontic palatal expander 10 also includes split beams 16. Split beams 16 are between first shells 12A and second shell 12B and are force applying members during the palatal expansion treatment. As best seen in FIGS. 1D-1F, each split beam of split beams 16 includes a first beam, a second beam and a space between the first and second beams. In the example of FIGS. 1A-1F, only first beam 20A, second beam 20B, and space 22 for first split beam 16A are labelled; however, each split beam of split beams 16 includes a similar first beam, second beam, and space between the first and second beams.

Each of first beam 20A and second beam 20B (collectively, "beams 20") may be formed from a relatively high modulus material. The relatively high modulus material may enable beams 20 to store energy in response to deformation and exert forces on shells 12. For example, orthodontic palatal expander 10 may be formed with a shape corresponding to a desired position of first and second posterior segments, and the patient or a provider may deform orthodontic palatal expander 10 when installing orthodontic palatal expander 10 on the teeth of the patient. The deformation may be concentrated in split beams 16, and may generate the energy released by split beams 16 in the form of forces on shells 12.

The relatively high modulus material from which beams 20 are formed may include, for example, one or more biocompatible polymers, a biocompatible metal, or the like. In some implementations, beams 20 may include the same biocompatible polymer used to form shells 12, and beams 20 may be integrally formed with shells 12, e.g., using 3D printing, thermoforming, molding or sculpting, or the like. In other examples, beams 20 may be formed separately from shells 12 and attached to shells 12. For example, beams 20 may be thermoformed in layers and attached to their neighboring components (e.g., shells 12 or one of shells 12 and connecting plate 18), fabricated from metal wire using a wire-bending robot, hand-formed according to a 2D image or 3D template, bent in 2D according to a program by sandwiching between a plurality of computer-actuated shims or fingers, or laser-cut or milled to a 2D form from a sheet of metal. In examples in which beams 20 include a biocompatible metal, beams 20 may include, for example, stainless steel, titanium, a nickel-titanium alloy, or another alloy used to make orthodontic archwires or other orthodontic appliances.

Split beams 16 also include space 22 between beams 20. Space 22 may be left open (e.g., devoid of material) or may be at least partially filled with a relatively low modulus material. The relatively low modulus material may be more flexible than the material from which beams 20 are formed, which may allow relative movement between beams 20 with relatively little resistance. Leaving space 22 devoid of material offers less resistance to relative movement between beams 20, but may allow food to become trapped between beams 20. At least partially filling space 22 with a relatively low modulus material may reduce or eliminate food becoming trapped between beams 20, but may offer some resistance to movement between beams 20. The relatively low modulus material may include, for example, a biocompatible elastomeric material, such as a silicone rubber, a polyurethane elastomer, a polycarbonate urethane elastomer, an acrylic elastomer, or the like.

In this way, each split beam of split beams 16 may be similar to a laminated beam or I-beam that includes parallel flanges (beams 20) and a shear web, but may omit the shear web or form the shear web with a relatively low modulus, elastomeric material. This configuration may allow for a relatively large amount of deflection of split beams 16 while allowing control of the magnitude and direction of rotation at the ends of beams 20, e.g., by controlling relative lengths of the beams 20, attachment points of the respective ends of the beams 20 to other structures, such as shells 12 or connecting plate 18, or the like. For example, by forming beams 20 to have respective lengths and attachment points so that beams 20 and the surfaces to which beams 20 attach define a parallelogram, the shells 12 will expand in a horizontal plane parallel to the occlusal plane as beams 20 exert forces on the shells 12, which may cause or allow a third-order rotation of shells 12 and, ultimately, a third-order rotation of the teeth received by shells 12 about a horizontal axis parallel to the occlusal plane and extending in a mesial-distal direction. On the other hand, by forming beams 20 to have respective lengths and attachment points so that beams 20 and the surfaces to which beams 20 attach define a trapezoid, the ends of beams 20 may rotate in opposite directions as beams 20 exert forces on shells 12, which may counteract reaction torque of teeth received by shells 12 due to displaced centers of rotation of the at least one teeth of the first posterior segment and at least one teeth of the second posterior segment. In this way, split beam 16 may enable control over third-order rotation of the at least one teeth of the first posterior segment and at least one teeth of the second posterior segment about a horizontal axis parallel to the occlusal plane and extending in a mesial-distal direction (e.g., tipping of tooth crowns in a bucco-lingual direction). This is a contrast to a solid beam, in which bending occurs along the entire length of the solid beam with rotation at the beam end occurring along an arc whose radius is approximately the length of the beam, i.e., whose bending radius is approximated as the length of a cantilevered beam fixed at one end and free at the other end. As such, a solid beam may result in unwanted torque rotations of the teeth, thus tipping the teeth buccally about their root centers without much whole-body translation.

In some examples, the two beams of a single split beam (e.g., beams 20 of split beam 16A) may be substantially parallel (e.g., parallel or nearly parallel) to each other. In other examples, the two beams of a single split beam may not be parallel to each other. Similarly, the connections of two beams of a single split beam to one of shells 12 may be substantially vertical (e.g., vertical or nearly vertical), or may be non-vertical. In general, the shape of a quadrilateral defined by the two beams of a split beam and the surfaces to which the ends of the beams attach may be selected to control rotation of teeth received by shells 12, e.g., about a horizontal axis parallel to the occlusal plane and extending in a mesial-distal direction.

Each of beams 20 may define a cross-sectional shape in a plane perpendicular to a length of the respective beam. The cross-sectional shape may affect flexibility/rigidity of the beam in different directions. For example, a greater thickness in a certain dimension may result in less flexibility in that dimension, which may increase a force generated for a given deformation but may reduce a length over which the force is expressed. Conversely, a lesser thickness in a certain dimension may result in greater flexibility in that dimension, which may decrease a force generated for a given deformation but may increase a length over which the force is expressed. In this way, selecting the cross-sectional shape of each beam of beams 20 may affect a magnitude and direction of the force applied by the respective beam. Example cross-sectional shapes for beams 20 include rectangular, rounded rectangular (including square and rounded square), circular, elliptical, superelliptical, or the like.

Similarly, a diameter of each respective beam in a given dimension of the respective beam may be selected to affect a magnitude and direction of the force applied by the respective beam. For example, each of the beams may define a thickness in at least one dimension of the cross-section of between about 0.2 mm and about 3 mm, such as between about 0.5 mm and about 2 mm, or about 1 mm.

The dimension of space 22 also may affect the axis of rotation of shells 12. As such, the dimension of space 22 in a plane perpendicular to a length of the split beam may be selected to affect the rotation of shells 12. In some examples, a dimension of space 22 in a plane perpendicular to a length of the split beam may be infinitesimally small (i.e., a number greater than 0) to about 10 mm, such as about 0.01 mm to about 2.0 mm, or about 0.5 mm.

In some examples, orthodontic palatal expander 10 may include connecting plate 18. In some examples, as shown in FIGS. 1A-1F, connecting plate 18 may be configured to be positioned adjacent to the palate of the patient. In other examples, as described below with reference to FIG. 3, a connecting plate may be configured to be positioned adjacent to anterior teeth of a dental arch of the patient.

Connecting plate 18 includes a structure to which one end of each of split beams 16 is attached. The opposite end of each of split beams 16 is attached to one of shells 12. In this way, connecting plate 18 functions as a support member against which split beams 16 push when exerting forces on shells 12.

In some examples, connecting plate 18 is formed from a relatively high modulus material, similar to beams 20. For example, connecting plate 18 may be formed from one or more biocompatible polymers, a biocompatible metal, a non-biocompatible metal coated with a biocompatible metal or polymer, or the like. In some implementations, connecting plate 18 may include the same biocompatible polymer used to form shells 12 and beams 20, and connecting plate 18, beams 20, and shells 12 may be integrally formed, e.g., using 3D printing, thermoforming, molding or sculpting, or the like. In other examples, connecting plate 18 may be formed separately from shells 12, beams 20, or both, and attached to beams 20. For example, connecting plate 18 may be thermoformed in layers and attached to beams 20, hand-formed according to a 2D image or 3D template, bent in 2D or 3D according to a program by sandwiching between a plurality of computer-actuated shims or fingers, or laser-cut or milled to a 2D form from a sheet of metal. In examples in which connecting plate 18 includes a biocompatible metal, connecting plate 18 may include, for example, stainless steel, titanium, a nickel-titanium alloy, or another alloy used to make orthodontic archwires or other orthodontic appliances. In examples in which connecting plate 18 includes non-biocompatible metal, the coating may include a biocompatible metal such as gold, rhodium, palladium, platinum, silver, copper, or the like, a biocompatible polymer such as poly(tetrafluoroethylene); polyethylene; parylene; an acrylic; an epoxy; a silicone; a polyester; a polyurethane; a polycarbonate; a thiol-ene polymer; an acrylate polymer, such as an urethane (meth)acrylate, a polyalkylene oxide di(meth)acrylate, an alkane diol di(meth) acrylate, an aliphatic (meth)acrylate, or a silicone (meth) acrylate; a polyethylene terephthalate based polymer, such as polyethylene terephthalate glycol (PETG); or the like. In some examples, the biocompatible polymer may be 3D printed, molded, or otherwise formed around the non-biocompatible metal.

Connecting plate 18 may define a thickness that, combined with the modulus of the material from which connecting plate 18 is formed, provides sufficient rigidity to anchor beams 20. For example, connecting plate 18 may define a thickness between about 1.5 mm and about 5 mm, such as between about 2.5 mm and about 3.0 mm.

The spacing of connecting plate 18 from the palate of the patient when orthodontic palatal expander 10 is in an undeformed state may be selected to allow for unimpeded movement of connecting plate 18 toward the palate in response to a force being applied to shells 12 to allow application of orthodontic palatal expander 10 to the teeth of the patient. For example, as shells 12 are urged inward to allow application of orthodontic palatal expander 10 to the teeth of the patient, connecting plate 18 may move upwards, toward the palate. As split beams 16 exert force on shells 12 to cause movement of the first and second posterior segments and opening of the palate, connecting plate 18 may move away from the palate as split beams 16 relax. The amount of vertical gap needed can be computed from the vertical separation of the beams 20 and the distance between connecting plate 18 and shells 12 (assuming a symmetrical configuration between the left and right quadrants of the arch).

In the example shown in FIGS. 1A-1F, orthodontic palatal expander 10 includes six split beams 16, three split beams 16-C between connecting plate 18 and first shell 12A and three split beams 16D-16F between connecting plate 18 and second shell 12B. In other examples, orthodontic palatal expander 10 may include more or fewer split beams 16. In general, orthodontic palatal expander 10 may include at least one split beam.

The number and relative size of split beams 16 may be selected to control application of force to shells 12, and may affect an axis of rotation of shells 12A and 12B. For example, by selecting first split beam 16A to be disproportionately longer or disproportionately shorter than third split beam 16C, split beams 16A-16C may cause a first order rotation of the first posterior segment received by first shell 12A as it translates in a buccal direction. The direction of rotation (e.g., clockwise, counterclockwise, or no rotation) may be selected based on the relative lengths and attachment points of split beams 16A-16C for the first posterior segment and split beams 16D-16F for the second posterior segment.

In some examples, the number and construction of split beams 16 may be selected to generate a force of between about 450 grams and about 900 grams against shells 12, which may achieve about 0.5 mm and about 1.0 mm per week of expansion of the palate of the patient.

In some examples, orthodontic palatal expander 10 may be configured to be temporarily affixed to the teeth received by first shell 12A and second shell 12B. For example, a moderately weak adhesive, such as a band cement, may be used to affix shells 12 to the respective teeth of the posterior segments. In other examples, orthodontic palatal expander 10 may be configured to be patient-removable.

Although FIGS. 1A-1F illustrate orthodontic palatal expander 10 as including connecting plate 18, in other examples, orthodontic palatal expander 10 may omit connecting plate 18, and split beams 16 may be directly connected between he first shell 12A and second shell 12B. In some such examples, space 22 may be present between split beams 16 near their mid-section. In other such examples, the dimension of space 22 may approach zero near the midsection of split beams 16 such that first and second beams 20A and 20B touch but are not connected.

Similarly, although FIGS. 1A-1F illustrate orthodontic palatal expander 10 including a first shell 12A and a second shell 12B that are each contiguous around the at least one posterior teeth, in other examples, one or both of first shell 12A and second shell 12B may be separated into two or more shells. For example, first shell 12A may be separated into a first, molar shell that receives a second molar of the first posterior segment and a second, bicuspid shell that receives a first bicuspid of the first posterior segment. The first, molar shell may be connected to connecting plate 18 or second shell 12B (or a first, molar shell of second shell 12B) via a first split beam. Similarly, the second, bicuspid shell may connected to connecting plate 18 or second shell 12B (or a second, bicuspid shell of second shell 12B) via a second split beam. The use of separate shells for the second molar and the first bicuspid is merely one example of the manner in which individual shells may receive individual posterior teeth and be connected to a split beam; other examples are also contemplated.

In this way, by including split beams 16, orthodontic palatal expander 10 may facilitate more precise control of rotational forces applied to shells 12 during expansion of orthodontic palatal expander 10.

Figure 2A:
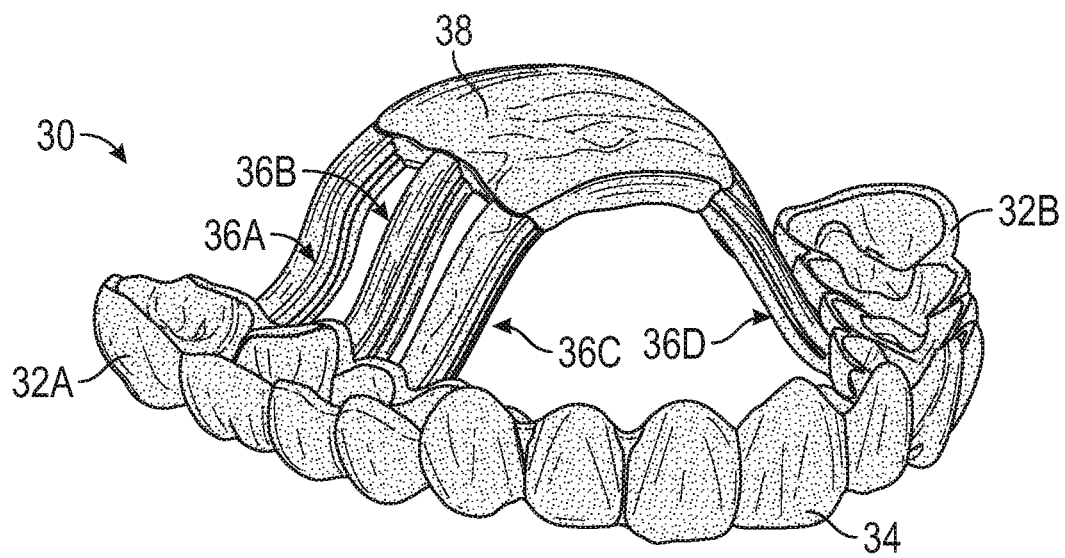
FIG. 2A is a facial-oblique view of an example hybrid orthodontic palatal expander and alignment tray.
Figure 2B:
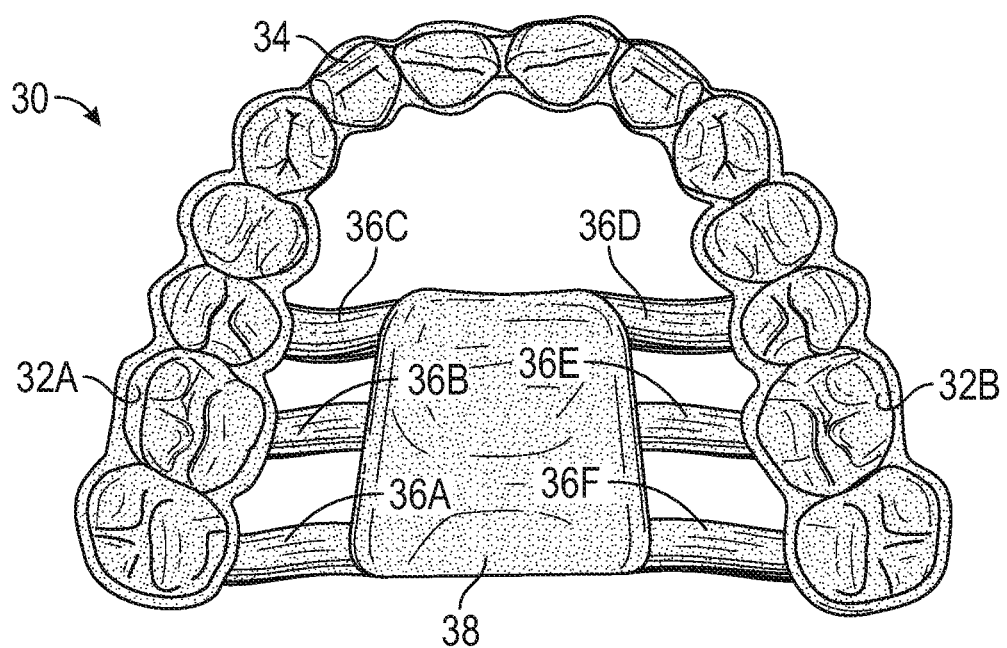
FIG. 2B is a gingival view of the example hybrid orthodontic palatal expander and alignment tray of FIG. 2A.
Figure 2C:
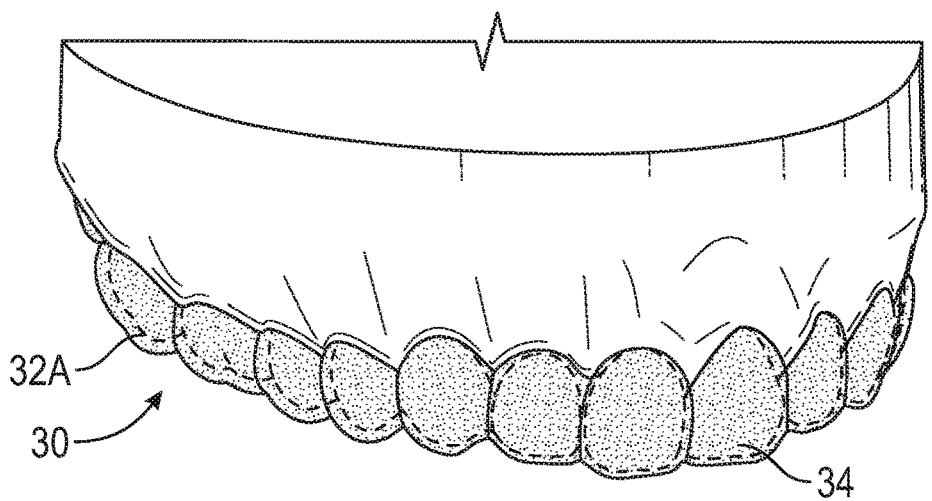
FIG. 2C is an oblique facial view of the example hybrid orthodontic palatal expander and alignment tray of FIG. 2A installed on a dental arch of a patient.

In some examples, as shown in FIGS. 1A-1F, orthodontic palatal expander 10 leaves anterior teeth 14 uncovered. In other examples, as shown in FIGS. 2A-2C, orthodontic palatal expander 10 may include or be integrated with an alignment tray that receives at least one anterior tooth 14 of the patient. FIG. 2A is a facial-oblique view of an example hybrid orthodontic palatal expander and alignment tray 30. FIG. 2B is a gingival view of hybrid orthodontic palatal expander and alignment tray 30. FIG. 2C is an oblique facial view of hybrid orthodontic palatal expander and alignment tray 30 installed on a dental arch of a patient.

Hybrid orthodontic palatal expander and alignment tray 30 may reduce a total treatment time by overlapping the palatal expansion period with the tooth alignment period. Additionally, or alternatively, hybrid orthodontic palatal expander and alignment tray 30 may reduce a total treatment time by overlapping the retention period after active expansion with the tooth alignment period. For example, up to about 3 months of retention time may be included after expansion to allow for ossification of bone in the mid-palatal suture. Active expansion may be prescribed for only a few weeks, but the expander may be left in place as a passive retainer for the retention period. Alternatively, the active expander may be replaced with a passive expander that is configured to reposition individual teeth but not to expand the palate. Such an appliance may include monolithic (not split) beams configured to maintain positions of posterior teeth, rather than to cause movement of posterior teeth. With slow palatal expansion, the line between active expansion and retention is blurred, but to good effect. While some orthodontists prefer to complete the expansion process all the way through retention before correcting tooth positions with braces, others install braces at the end of the active expansion period or even at its outset. With traditional braces, this requires a somewhat more complicated assemblage of appliances, and the bulk of hardware installed in the patient's mouth is doubled. The daily chore of brushing and flossing around so many intricate parts should not be underestimated, especially given the young age of a typical patient undergoing this form of treatment. Hybrid orthodontic palatal expander and alignment tray 30 may reduce this burden on the patient, as hybrid orthodontic palatal expander and alignment tray 30 may be removable and less bulky than traditional braces.

Hybrid orthodontic palatal expander and alignment tray 30 includes first posterior shell 32A, second posterior shell 32B, anterior shell 34, split beams 36A-36F (collectively, "split beams 36"), and optionally includes connecting plate 38. In some examples, each of first posterior shell 32A, second posterior shell 32B, split beams 36, and optional connecting plate 38 may be similar to or substantially the same as corresponding structures in orthodontic palatal expander 10 of FIG. 1.

Anterior shell 34 may be an alignment tray configured to receive anterior teeth and apply a force to one or more of the anterior teeth to reposition the one or more teeth. Anterior shell 34 is designed to be more resilient than posterior shells 32 and allow for deformation to occur upon installation, thereby exerting restorative forces on individual anterior teeth needed to move them relative to one another in the arch. In contrast, posterior shells may be configured to brace the teeth of the posterior segments during expansion and hold the relative positions of the teeth within the quadrant fixed. As such, posterior shells 32 may have walls with a greater thickness than anterior shell 34. For example, posterior shells 32 may include walls that are greater than about 1 mm thick, such as up to 4 or 5 mm thick, while anterior shell 34 may include walls that are about 0.2 mm to about 2.0 mm thick, such as about 0.3 mm to 1.0 mm thick.

The expansion portion of hybrid orthodontic palatal expander and alignment tray 30 (including posterior shells 32, split beams 36, and optional connecting plate 38) is activated by squeezing the buccal surfaces of posterior shells 32 together using finger pressure and holding the appliance in compression during insertion. The amount of compression will vary depending on the total amount of palatal expansion that is prescribed by hybrid orthodontic palatal expander and alignment tray 30 and the amount of expression remaining in hybrid orthodontic palatal expander and alignment tray 30. Regardless, hybrid orthodontic palatal expander and alignment tray 30 should be compressed enough to cause the posterior shells 32 to align with the corresponding teeth. Once aligned and loosely seated, finger pressure is applied to the occlusal surfaces of hybrid orthodontic palatal expander and alignment tray 30, both posterior and anterior, to fully seat hybrid orthodontic palatal expander and alignment tray 30 onto the teeth. Once seated, there should be little to no stress in the posterior shells 32, but the anterior shell 34, by design, will not fit the anterior teeth perfectly. The deformation in anterior shell 34 exerts forces on individual anterior teeth to urge them into their intended positions.

Hybrid orthodontic palatal expander and alignment tray 30 may help control or correct a large diastema between the upper central incisors that otherwise may develop during palatal expansion. In this way, closure can be maintained during the expansion process. This is harder to achieve automatically with conventional braces due to sliding mechanics between the brackets and archwire. Elastic power-chains are often needed with conventional braces to maintain closure during expansion if the arch is not very crowded.

In some examples, rather than anterior shell 34 being unitary, there may be a discontinuity or division between left and right portions of anterior shell 34. Similarly, posterior shells 32 may extended more toward the anterior teeth, such as up to and including the central incisors, while varying in thickness. For example, posterior shells 32 may become thinner at the more anterior teeth. In this way, the posterior teeth in the segment can serve as anchors while the anterior teeth can be individually repositioned.

In some examples, posterior shells 32 may be modified to facilitate individual repositioning of one or more posterior teeth by thinning the respective posterior shell in a selected area corresponding to a posterior tooth to allow for greater resiliency and application of force to the posterior tooth. In some examples, a split beam may be omitted from the portion of posterior shells 32 being used to reposition a posterior tooth to relieve expansion forces and allow localized forces exerted by the more resilient portion to reposition the posterior tooth.

In some examples, instead of including a connecting plate that is configured to be positioned adjacent to the palate of the patient, a connecting plate may be configured to be positioned adjacent to lingual surface or a labial surface of anterior teeth of the patient. For example, FIG. 3 is a partial oblique view of another example orthodontic palatal expander 40 including split beams 46 installed on a dental arch of a patient.

Orthodontic palatal expander 40 includes first posterior shell 42A, a second posterior shell (not shown in FIG. 3), a first split beam 46A, a second split beam (not shown in FIG. 3), and, optionally, connecting plate 48. Split beam 46A includes first beam 50A, second beam 50B, and space 52 between first beam 50A and second beam 50B. Each of first posterior shell 42A, the second posterior shell, first split beam 46A, the second split beam, and optional connecting plate 48 may be similar to or substantially the same as corresponding structures in orthodontic palatal expander 10 of FIG. 1, aside from the differences described herein.

Unlike orthodontic palatal expander 10, first split beam 46A and the second split beam are configured to extend in a mesial-distal direction adjacent to lingual surfaces of anterior teeth 44. Similarly, connecting plate 48 is configured to be positioned adjacent to lingual surfaces of anterior teeth 44. As such, the arcuate forms of first split beam 46A and the second split beam lie in roughly a horizontal plane (parallel to the occlusal plane) instead of a vertical plane, and the split beams leave more room for the tongue against the palate, which may make it easier for the patient to swallow food.

Figure 3:
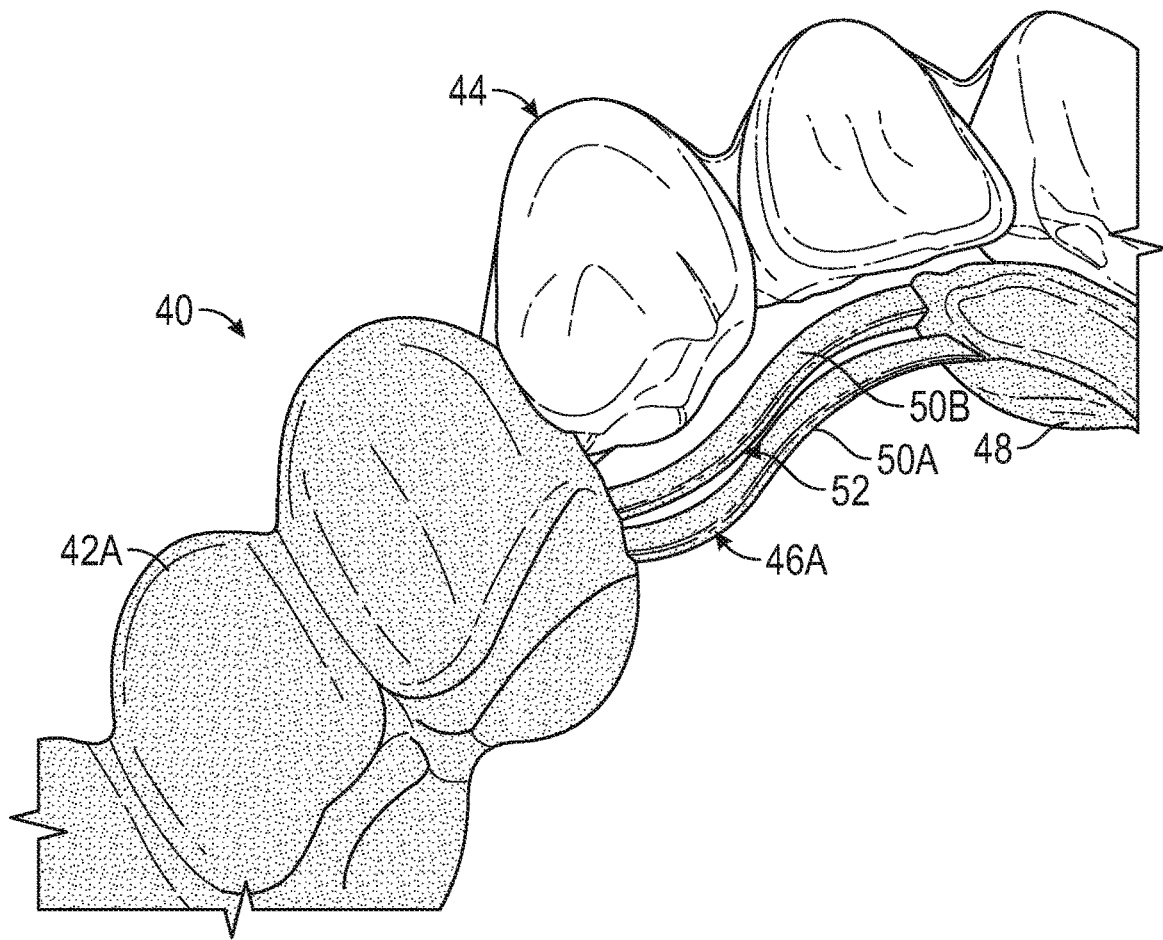
FIG. 3 is a partial oblique view of another example orthodontic palatal expander including split beams installed on a dental arch of a patient.

In the example shown in FIG. 3, a respective end of both beams 50 are connected to an anterior-most surface of first posterior shell 42A. However, in other examples, second beam 50B may be attached to the anterior-most portion of first posterior shell 42A, and first beam 50A may be attached to a more posterior portion of first posterior shell 42A, such as a portion of first posterior shell 42A surrounding the first molar. Attaching first beam 50A to a more posterior portion of first posterior shell 42A may allow for more leverage, greater expression of buccal forces to expand the palate, or both. Similarly, first and second beams 50 may be attached to selected positions of connecting plate 48 to allow control of the force magnitude and direction exerted by first and second beams 50 on first posterior shell 42A. Similar considerations also apply for the second split beam and the second posterior shell, although they are not illustrated in FIG. 3.

The relative points of attachment of the ends of beams 50 to first posterior shell 42A and connecting plate 48 affect the magnitude and direction of the applied force, similar to the description above with respect to FIG. 1. For example, if the 4 attachment points of first split beam 46A form a parallelogram configuration, then connecting plate 48 will translate at a right angle to first posterior shell 42A (similar for the second posterior shell), and first posterior shell 42A will translate in a straight line away from the second posterior shell, remaining parallel. However, if the 4 attachment points of first split beam 46A form a trapezoid, then first posterior shell 42A will rotate and translate, resulting in a $1^{st}$ order rotation of the first posterior segment received by first posterior shell 42 as it translates in a buccal direction. Depending on the configuration and quadrant, the rotation could be clockwise or counter-clockwise. This effect can be used advantageously to counter-act rotational effects in the reaction forces of the teeth. For example, first split beam 46A attaches at the anterior end of first posterior shell 42A where first split beam 46A applies a rotating couple to the pair of attachment points. However, the center of resistance in first posterior shell 42a is somewhere in the middle of the first posterior segment, perhaps biased toward the middle of the $1^{st}$ molar, given that the molars have more root area than the bicuspids. This large displacement between the point of applied force and the center or resistance (reaction force) results in a couple that can lead to adverse rotation of the first posterior segment. This adverse rotation can be countered or substantially canceled out by applying a coupling force at the attachment points in the opposite direction of the reaction force. The result is a net translation of the arch segments without an adverse rotation.

In some examples, rather than split beam 46A and connecting plate 48 being positioned adjacent to a lingual surface of anterior teeth 44, first split beam 46A and connecting plate 48 (and the second split beam not shown in FIG. 3) may be positioned adjacent to a labial surface of anterior teeth 44, and first split beam 46A (and the second split beam) may extend from buccal walls of first posterior shell 42A (and the second posterior shell), respectively. Such an arrangement may provide additional space for a patient's tongue by removing the volume of appliance lingual of the patient's teeth.

Figure 4:
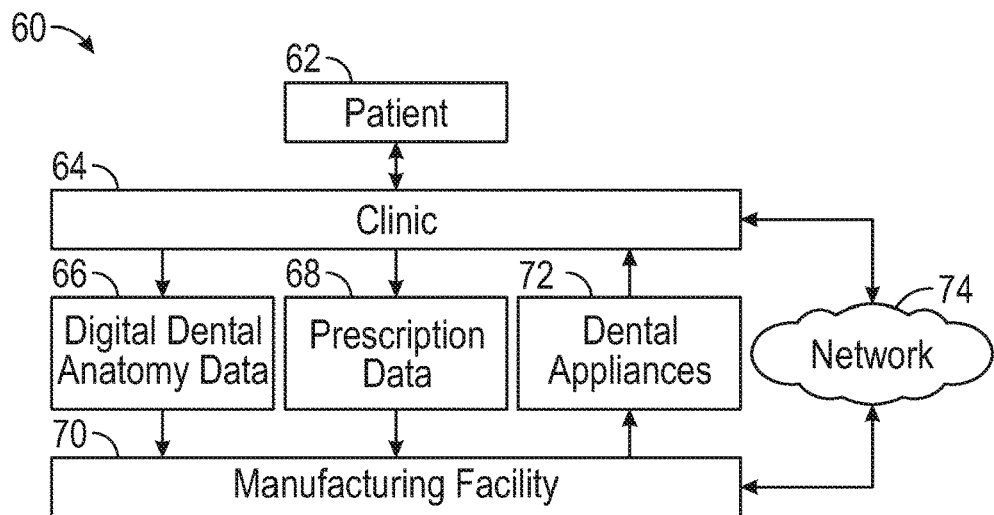
FIG. 4 is a block diagram illustrating an example computer environment in which a clinic and manufacturing facility communicate information throughout a dental appliance manufacturing process.

FIG. 4 is a block diagram illustrating an example computer environment 60 in which clinic 64 and manufacturing facility 70 communicate information throughout a manufacturing process of a set of orthodontic palatal expanders 72 for patient 12. The set of orthodontic palatal expanders 72 may include at least one of orthodontic palatal expanders 10, 30, or 40. As discussed above, orthodontic palatal expanders 10, 30, or 40 may include a first shell, a second shell, at least one split beam, and, optionally, a connecting plate. Initially, an orthodontic practitioner of clinic 64 generates one or more images of a dental anatomy of patient 62 using any suitable imaging technique and generates digital dental anatomy data 66 (e.g., a digital representation of tooth structure of patient 62). For example, the practitioner may generate X-RAY images that can be digitally scanned. Alternatively, the practitioner may capture digital images of the patient tooth structure using, for example, conventional computed tomography (CT), laser scanning, intra-oral scanning, CT scans of dental impressions, scans of dental casts poured from impressions, ultrasound instrumentation, magnetic resonance imaging (MRI), or any other suitable method of three-dimensional (3D) data acquisition. In other embodiments, the digital images may be provided using a hand-held intra-oral scanner such as the intra-oral scanner using active wavefront sampling developed by Brontes Technologies, Inc. (Lexington, Mass.) and described in PCT Publication No. WO 2007/084727 (Boerjes, et al.), which is incorporated by reference herein. Alternatively, other intra-oral scanners or intra-oral contact probes may be used. As another option, the digital dental anatomy data 66 may be provided by scanning a negative impression of teeth of patient 62. As still another option, the digital dental anatomy data 66 may be provided by imaging a positive physical model of teeth of patient 62 or by using a contact probe on a model of teeth of patient 62. The model used for scanning may be made, for example, by casting an impression of patient's 12 dentition from a suitable impression material such as alginate or polyvinylsiloxane (PVS), pouring a casting material (such as orthodontic stone or epoxy resin) into the impression, and allowing the casting material to cure. Any suitable scanning technique may be used for scanning the model, including those described above. Other possible scanning methods are described in U.S. Patent Publication No. 2007/0031791 (Cinader et al.), which is incorporated by reference herein.

In addition to providing digital images by scanning the exposed surfaces of the teeth, it is possible to image non-visible features of the dentition, such as the roots of teeth of patient 62 and jaw bones of patient 62. In some embodiments, the digital dental anatomy data 66 is formed by providing several 3D images of these features and subsequently "stitching" them together. These different images need not be provided using the same imaging technique. For example, a digital image of teeth roots provided with a CT scan may be integrated with a digital image of the teeth crowns provided with an intraoral visible light scanner. Scaling and registering of two-dimensional (2D) dental images with 3D dental images is described in U.S. Pat. No. 6,845,175 (Kopelman, et al.), which is incorporated by reference herein, and U.S. Patent Publication No. 2004/0029068 (Badura, et al.), which is also incorporated by reference herein. Issued U.S. Pat. No. 7,027,642 (Imgrund, et al.), which is incorporated by reference herein, and U.S. Pat. No. 7,234,937 (Sachdeva, et al.), which is also incorporated by reference herein, describe using techniques of integrating digital images provided from various 3D sources. Accordingly, the term "imaging" as it is used herein is not limited to normal photographic imaging of visually apparent structures, but includes imaging of dental anatomies that are hidden from view. The dental anatomy may include, but is not limited to, any portion of crowns or roots of one or more teeth of a dental arch, gingiva, periodontal ligaments, alveolar bone, cortical bone, implants, artificial crowns, bridges, veneers, dentures, orthodontic appliances, or any structure that could be considered part of the dentition before, during, or after treatment.

To generate digital dental anatomy data 66, a computer must transform raw data from the imaging systems into usable digital models. For example, for raw data representing the shapes of teeth received by a computer, the raw data is often little more than a point cloud in 3D space. Typically, this point cloud is surfaced to create 3D object models of the patient's dentition, including one or more teeth, gingival tissue, and other surrounding oral structure. For this data to be useful in orthodontic diagnosis and treatment, the computer may "segment" dentition surfaces to produce one or more discrete, movable 3D tooth object models representing individual teeth. The computer may further separate these tooth models from the gingiva into separate objects.

Segmentation allows a user to characterize and manipulate the teeth arrangement as a set of individual objects. Advantageously, the computer may derive diagnostic information such as arch length, bite setting, interstitial spacing between adjacent teeth, and even American Board of Orthodontics (ABO) objective grading from these models. As a further benefit, the digital orthodontic setups may provide flexibility in the manufacturing process. By replacing physical processes with digital processes, the data acquisition step and data manipulation steps can be executed at separate locations without the need to transport stone models or impressions from one location to another. Reducing or eliminating the need for shipping physical objects back and forth can result in significant cost savings to both customers and manufacturers of customized appliances.

After generating digital dental anatomy data 66, clinic 64 may store digital dental anatomy data 66 within a patient record in a database. Clinic 64 may, for example, update a local database having a plurality of patient records. Alternatively, clinic 64 may remotely update a central database (optionally within manufacturing facility 70) via network 74. After digital dental anatomy data 66 is stored, clinic 64 electronically communicates digital dental anatomy data 66 to manufacturing facility 70. Alternatively, manufacturing facility 70 may retrieve digital dental anatomy data 66 from the central database.

Clinic 64 may also forward prescription data 68 conveying general information regarding a practitioner's diagnosis and treatment plan for patient 62 to manufacturing facility 70. In some examples, prescription data 68 may be more specific. For example, digital dental anatomy data 66 may be a digital representation of the dental anatomy of patient 62. The practitioner of clinic 64 may review the digital representation and indicate at least one of desired movements, spacing, or final positions of individual teeth of patient 62. For example, the desired movements, spacing, and final positions of teeth of patient 62 may affect the forces to be applied to the teeth of patient 62 at each stage of treatment by each orthodontic palatal expander of the set of orthodontic palatal expanders 72. As discussed above, the forces applied by each orthodontic palatal expander (e.g., orthodontic palatal expanders 10, 30, or 40) of the set of orthodontic palatal expanders 72 may be determined by selecting the dimensions, shapes, and positions of the first and second shells, the at least one split beam, the optional connecting plate, and the optional alignment tray. In this way, digital dental anatomy data 66 may include practitioner selected dimensions, shapes, and positions of the first and second shells, the at least one split beam, the optional connecting plate, and the optional alignment tray of each of orthodontic palatal expander of the set of orthodontic palatal expanders 72 to result in the desired movement of the teeth of patient 62. Following review of the digital representation, the digital dental anatomy data 66 that includes the selected dimensions, shapes, and positions of the first and second shells, the at least one split beam, the optional connecting plate, and the optional alignment tray of each orthodontic palatal expander of the set of orthodontic palatal expanders 72 may be forwarded to manufacturing facility 70. Manufacturing facility 70 may be located off-site, or located with clinic 64.

For example, each clinic 64 may include its own equipment for manufacturing facility 70 such that a treatment plan and digital design may be performed entirely by a clinical practitioner, or an assistant, in the clinical setting, using software installed locally. The manufacturing may be performed in clinic 64, as well, by using a 3D printer (or by other methods of additive manufacturing). A 3D printer allows manufacturing of intricate features of a dental appliance or a physical representation of the dental anatomy of patient 62 through additive printing. The 3D printer may use iterative digital designs of original dental anatomy of patient 62 as well as a desired dental anatomy of patient 62 to produce multiple digital appliances and/or digital appliance patterns customized to produce the desired dental anatomy of patient 62. Manufacturing may include post-processing to remove uncured resin and remove support structures, or to assemble various components, which may also be necessary and could also be performed in a clinical setting.

Manufacturing facility 70 utilizes digital dental anatomy data 66 of patient 62 to construct the set of orthodontic palatal expanders 72 to reposition teeth of patient 62. Sometime thereafter, manufacturing facility 70 forwards the set of orthodontic palatal expanders 72 to clinic 64 or, alternatively, directly to patient 62. For example, the set of orthodontic palatal expanders 72 may be an ordered set of orthodontic palatal expanders. Patient 62 then wears the orthodontic palatal expanders 72 in the set of orthodontic palatal expanders 72 sequentially over time according to a prescribed schedule to reposition the teeth of patient 62 and expand the palate of patient 62. For example, patient 62 may wear each orthodontic palatal expander in the set of orthodontic palatal expanders 72 for a period of between about 2 weeks and about 12 weeks, such as between about 3 weeks and about 10 weeks or between about 4 weeks and about 8 weeks. Optionally, patient 62 may return to clinic 64 for periodic monitoring of the progress of the treatment with orthodontic palatal expanders 72.

During such periodic monitoring, a clinician may adjust the prescribed schedule of patient 62 for wearing the orthodontic palatal expanders in the set of orthodontic palatal expanders 72 sequentially over time. Monitoring generally includes visual inspection of the teeth and palate of patient 62 and may also include imaging to generate digital tooth structure data. In some relatively uncommon circumstances, the clinician may decide to interrupt the treatment of patient 62 with the set of orthodontic palatal expanders 72, for example, by sending the newly generated digital dental anatomy data 66 to manufacturing facility 70 in order to produce a new set of orthodontic palatal expanders 72. In the same or different examples, the clinician may send newly generated digital dental anatomy data 66 to manufacturing facility 70 following the completion of the prescribed schedule of the treatment with orthodontic palatal expanders 72. In addition, following the completion of the prescribed schedule of the treatment with orthodontic palatal expanders 72, the clinician may request a new set of orthodontic palatal expanders 72 from manufacturing facility 70 to continue treatment of patient 62.

Figure 5:
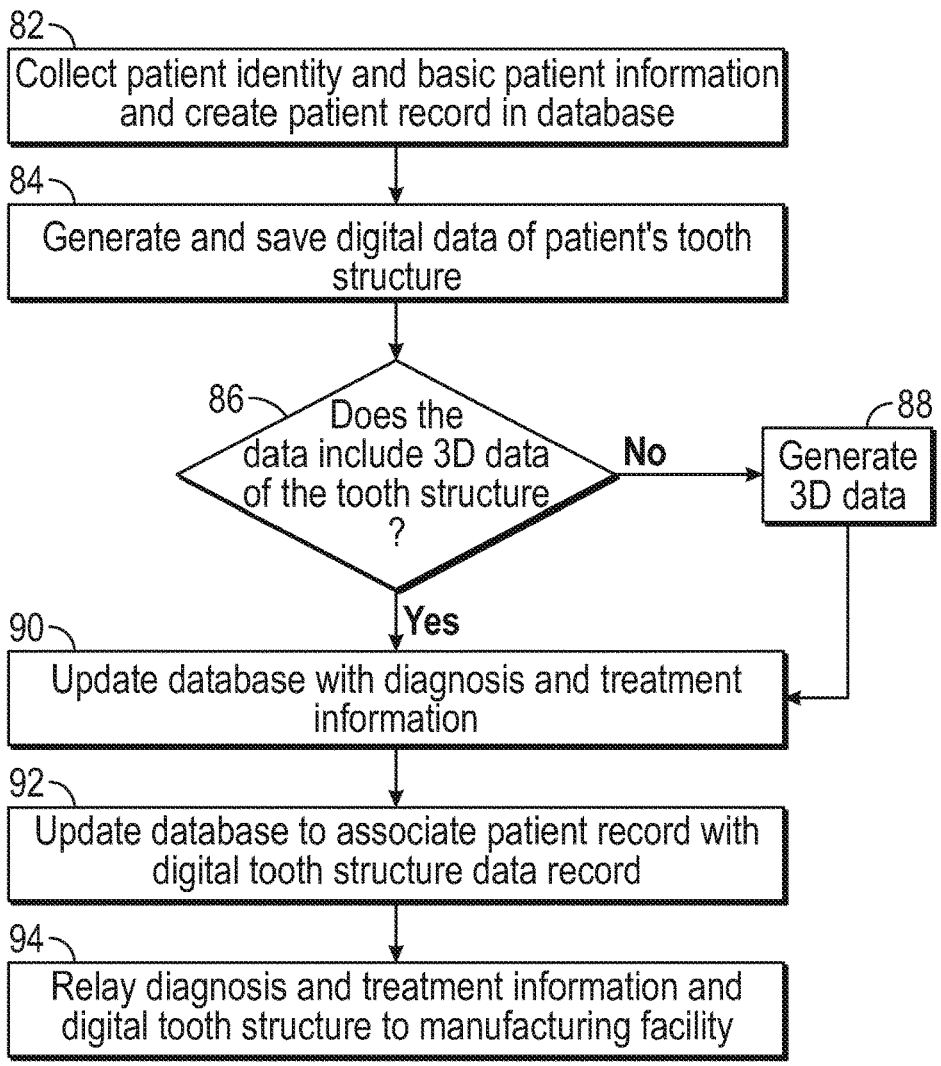
FIG. 5 is a flow diagram illustrating an example process of generating digital tooth structure data.

FIG. 5 is a flow diagram illustrating a process conducted at clinic 74 in accordance with one example of this disclosure. Initially, a practitioner at clinic 64 collects patient identity and other information from patient 62 and creates a patient record (82). As described, the patient record may be located within clinic 64 and optionally configured to share data with a database within manufacturing facility 70. Alternatively, the patient record may be located within a database at manufacturing facility 70 that is remotely accessible to clinic 64 via network 74 or within a database that is remotely accessible by both manufacturing facility 70 and clinic 64.

Next, digital dental anatomy data 66 of patient 62 may be generated using any suitable technique (84), to thereby create a virtual dental anatomy. Digital dental anatomy data 66 may include a two-dimensional (2D) image and/or a three-dimensional (3D) representation of the dental anatomy.

In one example, 3D representations of a dental anatomy are generated using a cone beam computerized tomography (CBCT) scanner, such as an i-CAT 3D dental imaging device (available from Imaging Sciences International, LLC; 1910 N Penn Road, Hatfield, Pa.). Clinic 64 stores the 3D digital dental anatomy data 66 (in the form of radiological images) generated from the CBCT scanner in the database located within clinic 64, or alternatively, within manufacturing facility 70. The computing system processes the digital dental anatomy data 66 from the CBCT scanner, which may be in the form of a plurality of slices, to compute a digital representation of the tooth structure that may be manipulated within the 3D modeling environment.

If 2D radiological images are used (86), then the practitioner may further generate 3D digital data (88). The 3D digital dental anatomy data 66 may be produced by, for example, forming and subsequently digitally scanning a physical impression or casting of the tooth structure of patient 62. For example, a physical impression or casting of a dental arch of patient 62 may be scanned using a visible light scanner, such as an OM-3R scanner (available from Laser Design, Inc. of Minneapolis, Minn.). Alternatively, the practitioner may generate the 3D digital dental anatomy data 66 of the occlusal service by use of an intra-oral scan of the dental arch of patient 62, or existing 3D tooth data. In one example, the method of forming a digital scan from a casting or an impression described in U.S. Pat. No. 8,491,306, titled, "REGISTERING PHYSICAL AND VIRTUAL TOOTH STRUCTURES WITH PEDESTALS," and issued on Jul. 23, 2013, which is incorporated herein by reference in its entirety, may be used. In the same or different examples, techniques for defining a virtual tooth surface and virtual tooth coordinate system as described in U.S. Patent Application Publication No. 2013/0325431, titled ORTHODONTIC DIGITAL SETUPS," and published on Dec. 5, 2013 may be used, which is incorporated herein by reference in its entirety. In any case, the digital data are digitally registered within the 3D modeling environment to form a composite digital representation of a tooth structure, which may include the tooth roots as well as the occlusal surfaces.

In one example, 2D radiological images and the 3D digital data for the occlusal surface of the dental arch are registered by first attaching registration markers (e.g., fiducial markers or a pedestal having known geometry) to the tooth structure of patient 62 prior to generating both the radiological images and the 3D digital scan. Thereafter, the digital representation of the registration markers within the 2D radiological image and the 3D digital data may be aligned within a 3D modeling environment using registration techniques described in U.S. Pat. No. 8,491,306.

In another example, 3D digital data of the tooth structure is generated by combining two 3D digital representations of the tooth structure. For example, a first 3D digital representation may be a relatively low-resolution image of the roots obtained from a CBCT scanner (e.g., an i-CAT 3D dental imaging device) and the second 3D digital representation may be a relatively high-resolution image of the crowns of the teeth obtained from an industrial CT scan of an impression or a visible light (e.g., laser) scan of a casting of the dental arch of the patient. The 3D digital representations may be registered using a software program that enables the 3D representations to be manipulated within a computer environment (e.g., Geomagic Studio software (available from 3D Systems, Inc.; 333 Three D Systems Circle, Rock Hill, S.C.), or alternatively, registration techniques described in U.S. Pat. No. 8,491,306 may be used.

Next, a computer system executing 3D modeling software renders a resultant digital representation of the tooth structure, including the occlusal surface as well as the root structure of the patient's dental arch. Modeling software provides a user interface that allows the practitioner to manipulate digital representations of the teeth in 3D space relative to the digital representation of the patient's dental arch. By interacting with the computer system, the practitioner generates treatment information, such as by selecting indications of the final positions of individual teeth and palate of patient 62, duration of a respective stage of treatment, or number of treatment stages, the direction or magnitude of forces on the teeth of patient 62 during a stage of treatment, or the like (90). For example, the final positions of individual teeth and the palate of patient 62, duration of a respective stage of treatment, or number of treatment stages may affect the direction or magnitude of forces on the teeth and the palate of patient 62 at each stage of treatment by each orthodontic palatal expander of the set of orthodontic palatal expanders 72. As discussed above, the forces applied by each orthodontic palatal expander of the set of orthodontic palatal expanders 72 may be determined by selecting the dimensions, shapes, and positions of the first and second shells, the at least one split beam, the optional connecting plate, and the optional alignment tray. In this way, updating the database with diagnostic and treatment information (90) may include determining or selecting by the practitioner the dimensions, shapes, and positions of the first and second shells, the at least one split beam, the optional connecting plate, and the optional alignment tray of each orthodontic palatal expander of the set of orthodontic palatal expanders 72 to result in the desired movement of the teeth of patient 62 and expansion of the palate of patient 62.

Once the practitioner has finished conveying general information regarding a diagnosis and treatment plan within the 3D environment, the computer system updates the database associated with the patient record to record the prescription data 68 conveying general information regarding a diagnosis and treatment plan as specified by the practitioner (92). Thereafter, the prescription data 68 is relayed to manufacturing facility 70 for manufacturing facility 70 to construct one or more orthodontic palatal expanders 72 (94).

Although described with respect to an orthodontic practitioner located at an orthodontic clinic, one or more of the steps discussed with respect to FIG. 5 may be performed by a remote user, such as a user located at manufacturing facility 70. For example, the orthodontic practitioner may only send radiological image data and an impression or casting of the patient to manufacturing facility 70, where a user interacts with a computer system to develop a treatment plan within a 3D modeling environment. Optionally, a digital representation of the treatment plan within the 3D modeling environment may then be transmitted to the orthodontic practitioner of clinic 64, who may review the treatment plan and either send back his or her approval, or indicate desired changes.

Figure 6:
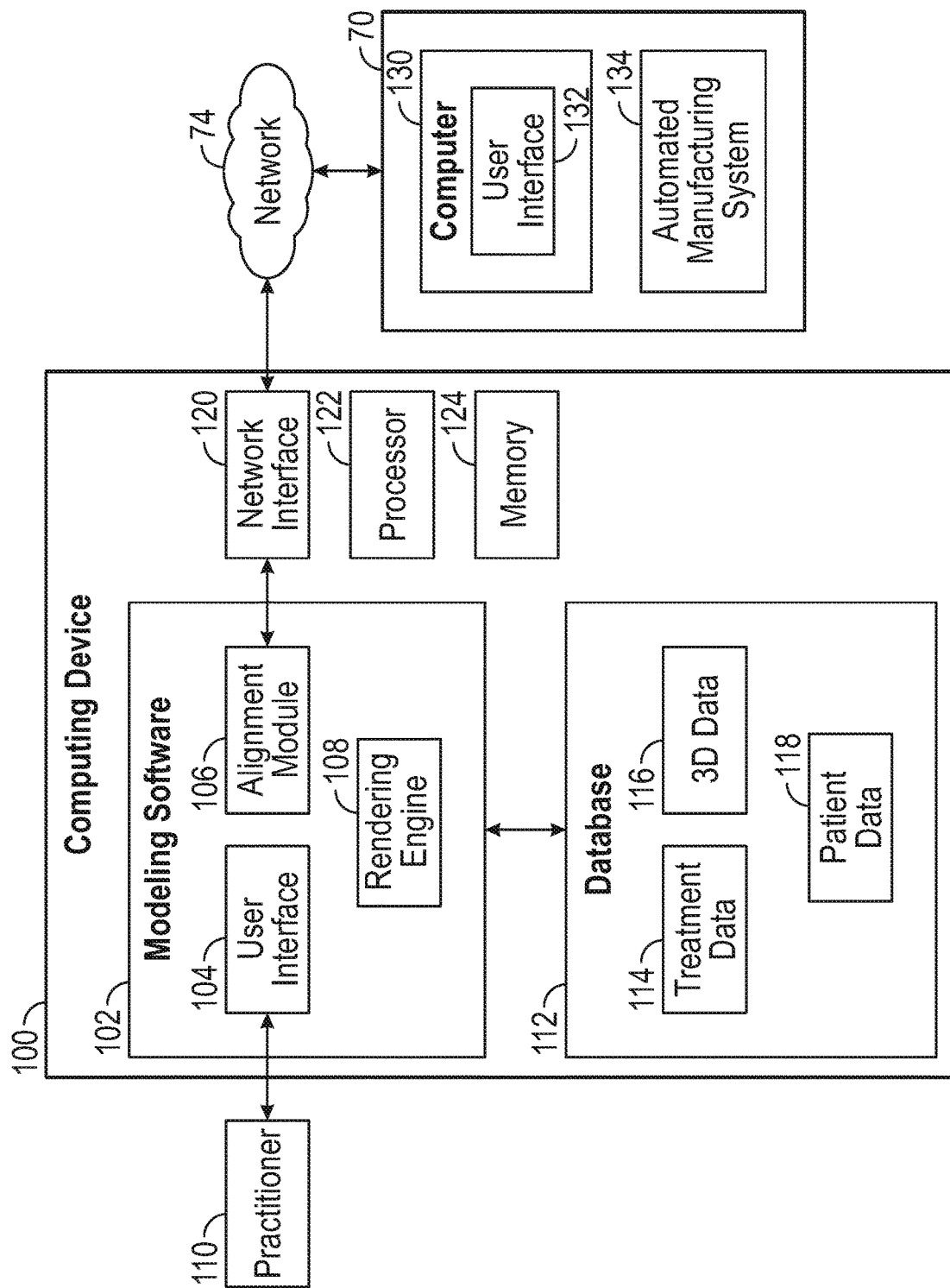
FIG. 6 is a block diagram illustrating an example of a client computing device connected to a manufacturing facility via a network to generate digital tooth structure data.

FIG. 6 is a block diagram illustrating an example of a computing device 100 connected to manufacturing facility 70 via network 74. In the illustrated example, computing device 100 provides an operating environment for modeling software 102. Modeling software 102 presents a modeling environment for modeling and depicting the 3D representation of the teeth of patient 62. In the illustrated example, modeling software 102 includes user interface 104, alignment module 106, and rendering engine 108.

User interface 104 provides a graphical user interface (GUI) that visually displays the 3D representation of teeth of patient 62. In addition, user interface 104 provides an interface for receiving input from practitioner 110 of clinic 64, e.g., via a keyboard and a pointing device, for manipulating teeth of patient 62 within the modeled dental arch.

Modeling software 102 may be accessible to manufacturing facility 70 via network interface 74. Modeling software 102 interacts with database 112 to access a variety of data, such as treatment data 114, 3D data 116 relating to the tooth structure of patient 62, and patient data 118. Database 112 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS) or object relational (ORDBMS) database management system. The data may, for example, be stored within a single relational database, such as SQL Server from Microsoft Corporation. Although illustrated as local to computing device 100, database 112 may be located remote from the computing device 100 and coupled to the computing device 100 via a public or private network, e.g., network 74.

Treatment data 114 describes diagnosis or repositioning information for the teeth of patient 62 selected by practitioner 110 and positioned within the 3D modeling environment. For example, treatment data 114 may include the dimensions, shapes, and positions of the first and second shells, the at least one split beam, the optional connecting plate, and the optional alignment tray that may result in a selected magnitude and direction of force vectors to be applied to teeth of patient 62 throughout the treatment plan.

Patient data 118 describes a set of one or more patients, e.g., patient 62, associated with practitioner 110. For example, patient data 118 specifies general information, such as a name, birth date, and a dental history, for each patient 62.

Rendering engine 108 accesses and renders 3D data 116 to generate the 3D view presented to practitioner 110 by user interface 104. More specifically, 3D data 116 includes information defining the 3D objects that represent each tooth (optionally including roots), and jaw bone within the 3D environment. Rendering engine 108 processes each object to render a 3D triangular mesh based on viewing perspective of practitioner 110 within the 3D environment. User interface 104 displays the rendered 3D triangular mesh to practitioner 110, and allows practitioner 110 to change viewing perspectives and manipulate objects within the 3D environment.

U.S. Pat. No. 8,194,067, titled, "PLANAR GUIDES TO VISUALLY AID ORTHODONTIC APPLIANCE PLACEMENT WITHIN A THREE-DIMENSIONAL (3D) ENVIRONMENT," issued on Jun. 5, 2012, and U.S. Pat. No. 7,731,495, titled, "USER INTERFACE HAVING CROSS SECTION CONTROL TOOL FOR DIGITAL ORTHODONTICS," issued on Jun. 8, 2010, describe other examples for computer systems and 3D modeling software having user interfaces that may be used with the techniques described herein, each of which are incorporated by reference in their entireties.

Computing device 100 includes processor 122 and memory 124 to store and execute modeling software 102. Memory 122 may represent any volatile or non-volatile storage elements. Examples include random access memory (RAM) such as synchronous dynamic random access memory (SDRAM), read-only memory (ROM), non-volatile random access memory (NVRAM), electrically erasable programmable read-only memory (EEPROM), and FLASH memory. Examples may also include non-volatile storage, such as a hard-disk, magnetic tape, a magnetic or optical data storage media, a compact disk (CD), a digital versatile disk (DVD), a Blu-ray disk, and a holographic data storage media.

Processor 122 represents one or more processors such as a general-purpose microprocessor, a specially designed processor, an application specific integrated circuit (ASIC), a field programmable gate array (FPGA), a collection of discrete logic, or any type of processing device capable of executing the techniques described herein. In one example, memory 74 may store program instructions (e.g., software instructions) that are executed by processor 122 to carry out the techniques described herein. In other examples, the techniques may be executed by specifically programmed circuitry of processor 122. In these or other ways, processor 122 may be configured to execute the techniques described herein.

Computing device 100 is configured to send a digital representation of a 3D tooth structure of a patient 62, and optionally, treatment data 114 and/or patient data 118 to computer 130 of manufacturing facility 70 via network 74. Computer 130 includes user interface 132. User interface 132 provides a GUI that visually displays the 3D representation of the digital model of teeth. In addition, user interface 132 provides an interface for receiving input from a user, e.g., via a keyboard and a pointing device, for manipulating a patient's teeth within the digital representation of the 3D tooth structure of the patient.

Computer 130 may further be configured to automatically determine dimensions and shapes of each orthodontic palatal expander of a set of orthodontic palatal expanders 72. The dimensions and shapes of orthodontic palatal expanders 72 may include a position, dimension, and shape of the first and second shells, the at least one split beam, the optional connecting plate, and the optional alignment tray such that orthodontic palatal expanders 72 are configured to reposition the one or more teeth and the palate from their initial positions to final positions when the orthodontic palatal expanders 72 are worn by the patient. As discussed above with respect to FIGS. 1-3, the position, dimension, and shape of the first and second shells, the at least one split beam, the optional connecting plate, and the optional alignment tray may affect the magnitude, direction, and length of expression of a force applied to the at least one teeth of the first and second posterior segments and, optionally, the anterior segment, when orthodontic palatal expanders 72 are worn by patient 62. For example, the thickness, shape, length, and attachment point of a respective beam of the at least one split beam may determine, at least in part, the magnitude, direction, and length of expression of the force resulting from a deformation of the respective beam when the removable dental appliance is worn by patient 62. Computer 130 may analyze at least one of the magnitude, direction, and length of expression of the force resulting from a deformation of the respective split beam or alignment tray when the orthodontic palatal expander is worn by the patient to determine at least one of position, dimension, and shape of the first and second shells, the at least one split beam, the optional connecting plate, and the optional alignment tray that will result in a desired movement of the teeth and palate of patient 62 when the orthodontic palatal expander is worn by patient 62.

Computer 130 may present a representation of orthodontic palatal expanders 72 for user to review, including review of dimensions and shapes. Alternatively, or additionally, computer 130 may accept input from a user to determine dimensions and shapes of a set of orthodontic palatal expanders 72 for patient 62. For example, the user input may influence at least one of an automatically determined dimensions or shapes. Computer 130 may transmit, or otherwise send, a digital model of the set of orthodontic palatal expanders 72, the dimensions and shapes of the set of orthodontic palatal expanders 72, or both, to automated manufacturing system 134 for production of the set of orthodontic palatal expanders 72.

Computer device 100 and computer 130 are merely conceptual representations of an example computer system. In some examples, the functionalities described with respect to computing device 100, computer 130, or both may be combined into a single computing device or distributed among multiple computing devices within a computer system. For example, cloud computing may be used for digital design of orthodontic palatal expanders described herein. In one example, the digital representations of tooth structures are received at one computer at the clinic, while a different computer, such as computer 130, is used to determine the shapes and dimensions of a orthodontic palatal expander. In addition, it may not be necessary for that different computer, such as computer 130, to receive all of the same data in order for it determine shapes and dimensions. Shapes and dimensions may be determined, at least in part, based on knowledge derived through analysis of historical cases or virtual models of exemplary cases, without receiving a complete 3D representation of the case in question. In such an example, data transmitted between computing device 100 and computer 130, or otherwise utilized to design a custom dental appliance may be significantly less than the complete data set representing a complete digital dental model of a patient 62.

Figures 7, 8:
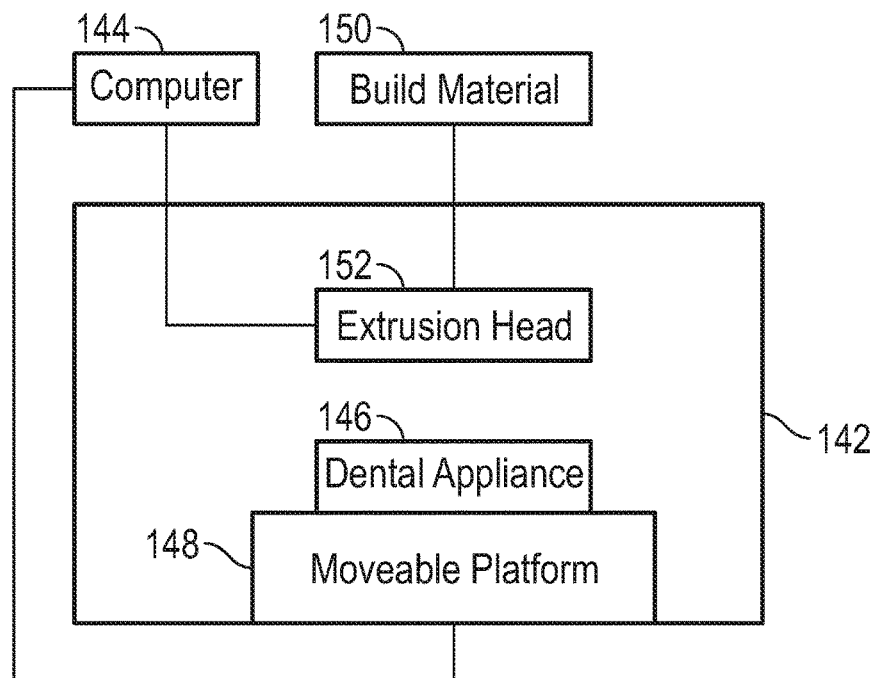
FIG. 7 is a block diagram illustrating an example computer-aided manufacturing system for construction of an orthodontic palatal expander.
FIG. 8 is a flow diagram illustrating a process conducted at a manufacturing facility for construction of a set of orthodontic palatal expanders.

FIG. 7 is a block diagram illustrating an example computer-aided manufacturing system 140 for construction of removable dental appliance 146. Computer-aided manufacturing system 140 may include an additive manufacturing system 142 in communication with computer 144 and coupled to build material source 150. Computer-aided manufacturing system 142 may be an example of automated manufacturing system 134 of FIG. 6. For example, computer 144 may be the same as or substantially similar to computer 130.

Build material source 150 may include a source of at least one polymeric material, such as, for example, at least one of the polymeric materials of a orthodontic palatal expander, discussed above. Dental appliance 146 may be the same as or substantially similar to at least one of orthodontic palatal expanders 10, 30, and 40. In some examples, dental appliance 146 may include one dental appliance of set of dental appliances 146.

Additive manufacturing system 142 may include a moveable platform 148 and an extrusion head 152. Movable platform 148 and extrusion head 152 may be configured to manufacture dental appliance 146. For example, computer 144 may control extrusion head 152 and moveable platform 148 to manufacture dental appliance 146. Controlling, by computer 144, extrusion head 152 may include at least one of controlling a material feed rate from build material source 150 to extrusion head 152, controlling a deposition rate of build material on dental appliance 146, controlling a temperature of extrusion head 152, and controlling a position of extrusion head 152. By controlling at least one of a material feed rate, a material deposition rate, a temperature of extrusion head 152, and a position of extrusion head 152, computer 144 may control manufacture of a position, dimension, and shape of dental appliance 146. Controlling, by computer 144, movable platform 148 may include at least one of controlling a translation of moveable platform in a plane normal to the direction of material deposition from extrusion head 152 and controlling an elevation of moveable platform along an axis substantially parallel to the direction of material deposition from extrusion head 152. By controlling at least one of a translation and elevation of moveable platform 148, computer 144 may control manufacture of a position, dimension, and shape of dental appliance 146.

Although FIG. 7 illustrates a computer-aided manufacturing system 140 configured for Fused Deposition Modeling (FDM), computer-aided manufacturing system 140 may also be configured for stereolithography (SLA), inverse vat polymerization additive manufacturing, or inkjet/polyjet additive manufacturing. In examples in which computer-aided manufacturing system 140 is configured for polyjet printing, computer-aided manufacturing system 140 may be configured to print multiple materials in a single print, thereby allowing a high modulus material for the rigid components of orthodontic palatal expanders 72 and a low modulus or elastomeric material for the space between the split beams of orthodontic palatal expanders 72. Further, with polyjet additive manufacturing, the modulus may be varied selectively across the orthodontic palatal expanders 72, and a different modulus may be used for the split beams than is used for the shells, for example. Similarly, a different modulus may be used for the anchoring posterior shells than is used for the anterior shell used to reposition individual teeth.

FIG. 8 is a flow diagram illustrating a process conducted at manufacturing facility 70 (FIG. 4) for construction of set of orthodontic palatal expanders 72. In some examples, set of orthodontic palatal expanders 72 may include at least one of orthodontic palatal expanders 10, 30, and 40. Computer 130 at manufacturing facility 70 receives digital dental anatomy data 66 including initial positions of one or more teeth of the patient and prescription data 68 from clinic 64 (162). Alternatively, computer 130 may retrieve the information from a database located within or otherwise accessible by computer 130. A trained user associated with computer 130 may interact with a computerized modeling environment running on computer 130 to develop a treatment plan relative to the digital representation of the patient's tooth structure and generate prescription data 68, if clinic 64 has not already done so. In other examples, computer 80 may automatically develop a treatment plan based solely on the patient's tooth structure and predefined design constraints.

Once computer 130 receives patient's tooth structure, computer 130 determines dimensions and shapes of a orthodontic palatal expander 72 for patient 62 (164). The dimensions and shapes of orthodontic palatal expander 72 are configured to reposition the one or more teeth and the palate of patient 62 from their initial positions to intermediate or final positions when orthodontic palatal expander 72 is worn by patient 62. In the same or additional examples, computer 130 determines dimensions and shapes of set of orthodontic palatal expanders 72 for patient 62 configured to be worn in series.

In some examples, determining dimensions and shapes of orthodontic palatal expander 72 includes selecting, with computer 130, the dimensions and shapes of the orthodontic palatal expander 72 according to a set of predefined design constraints. The set of predesigned design constraints may include one or more factors, including, but not limited to, at least one of a minimum and a maximum localized force applied to one or more of the surrounded teeth, at least one of a minimum and a maximum rotational force applied to one or more of the surrounded teeth, at least one of a minimum and a maximum translational force applied to one or more of the surrounded teeth, at least one of a minimum and a maximum total force applied to one or more of the surrounded teeth, and at least one of minimum and a maximum stress or strain applied to the removable dental appliance, when the removable dental appliance is worn by the patient and the surrounded teeth are in their initial positions. Minimum applied forces are necessary to cause bone remodeling, tooth movement, and palatal expansion.

Computer 130 may use finite element analysis (FEA) techniques to analyze forces on a teeth of patient 62 as well as orthodontic palatal expander 72 during the determination of the dimensions and shapes of orthodontic palatal expander 72. For example, computer 130 may apply FEA to a solid model of the teeth of patient 62 as the modeled teeth move from their initial positions to their final positions representing a treatment including an ordered set of orthodontic palatal expanders 72. Computer 130 may use FEA to select appropriate dimensions and shapes of orthodontic palatal expanders 72 to apply the desired forces on the teeth. In addition, computer 130 may use a virtual articulator to determine contact points between the teeth throughout the movement of the modeled teeth during the treatment. Computer 130 may further include occlusal contact forces, such as cusp interdigitation forces, in the FEA forces analysis in combination with forces from orthodontic palatal expanders 72 during the design of orthodontic palatal expanders 72 in an ordered set of orthodontic palatal expanders 72.

In some examples, determining dimensions and shapes of orthodontic palatal expanders 72 includes selecting, with computer 130 thicknesses of orthodontic palatal expanders 72, such as the first and second shells, the beams of the at least one split beam, the optional connecting plate, and the optional alignment tray to provide a stiffness suitable to reposition the one or more teeth and the palate of patient 62 from their initial positions to final positions when orthodontic palatal expanders 72 are worn by patient 62. In some examples, computer 130 may further select materials for the various portions of orthodontic palatal expanders 72 according to the predefined design constraints.

The dimensions and shapes of a orthodontic palatal expander 72 for patient 62 may be presented to a user via user interface of 132 of computer 130 (166). In examples in which dimensions and shapes of orthodontic palatal expander 72 are presented to a user via user interface of 132, the user may have the opportunity to adjust the design constraints or directly adjust the dimensions and shapes of orthodontic palatal expander 72 before the design data is sent to automated manufacturing system 134. In some examples, the dimensions and shapes of orthodontic palatal expander 72 may be presented to a user by computer 130 directly as removable dental appliance is manufactured by automated manufacturing system 134. For example, computer 130 may send a digital model of orthodontic palatal expander 72 to computer-aided manufacturing system 134, and computer-aided manufacturing system 134 manufactures orthodontic palatal expander 72 according to the digital model from computer 130 (170).

However, even in examples where the dimensions and shapes of orthodontic palatal expander 72 for patient 62 may be presented to a user via user interface of 132 of computer 130, following user approval, computer 130 sends a digital model of orthodontic palatal expander 72 to automated manufacturing system 134 (168), and computer-aided manufacturing system 134 manufactures orthodontic palatal expander 72 according to the digital model from computer 130 (170).

In some examples, computer-aided manufacturing system 134 may include a 3D printer. Forming orthodontic palatal expander 72 may include printing the surfaces of orthodontic palatal expander 72 with the 3D printer. In other examples, forming orthodontic palatal expander 72 may include printing representations of the teeth of patient 62 with the 3D printer, thermoforming appliance body over the representations of the teeth, and trimming excess material to form the first and second shells, the at least one split beam, the optional connecting plate, and the optional alignment tray. In other examples, the beams of the at least one split beam may be thermoformed in layers and attached to their neighboring components (e.g., a shell and the connecting plate), fabricated from metal wire using a wire-bending robot, hand-formed according to a 2D image or 3D template, bent in 2D according to a program by sandwiching between a plurality of computer-actuated shims or fingers, or laser-cut or milled into a 2D form from a sheet of metal. The representations of the teeth of patient 62 may include raised surfaces to facilitate forming at least one of the first and second shells, the at least one split beam, the optional connecting plate, or the optional alignment tray in the thermoformed and trimmed appliance body.

The technique of FIG. 8 may be applied to design and manufacture of each orthodontic palatal expander of an ordered set of orthodontic palatal expanders 72. For example, each orthodontic palatal expander in the ordered set of orthodontic palatal expanders 72 may be configured to incrementally reposition the teeth of patient 62. In this manner, the ordered set of orthodontic palatal expanders 72 may be configured to reposition the teeth of patient 62 to a greater degree than any one of the orthodontic palatal expanders 72. Such an ordered set of orthodontic palatal expanders 72 may specifically be configured to incrementally reposition the one or more teeth of patient 62 from their initial positions to final positions as the orthodontic palatal expanders 72 of the ordered set of orthodontic palatal expanders 72 for patient 62 are worn sequentially by patient 62.

In some examples, the technique described with respect to FIG. 8 may be embodied within a computer-readable storage medium, such as a computer-readable storage medium of computing device 100, computer 130, or both. The computer-readable storage medium may store computer-executable instructions that, when executed, configure a processor to perform the techniques described with respect to FIG. 8.

Figure 9:
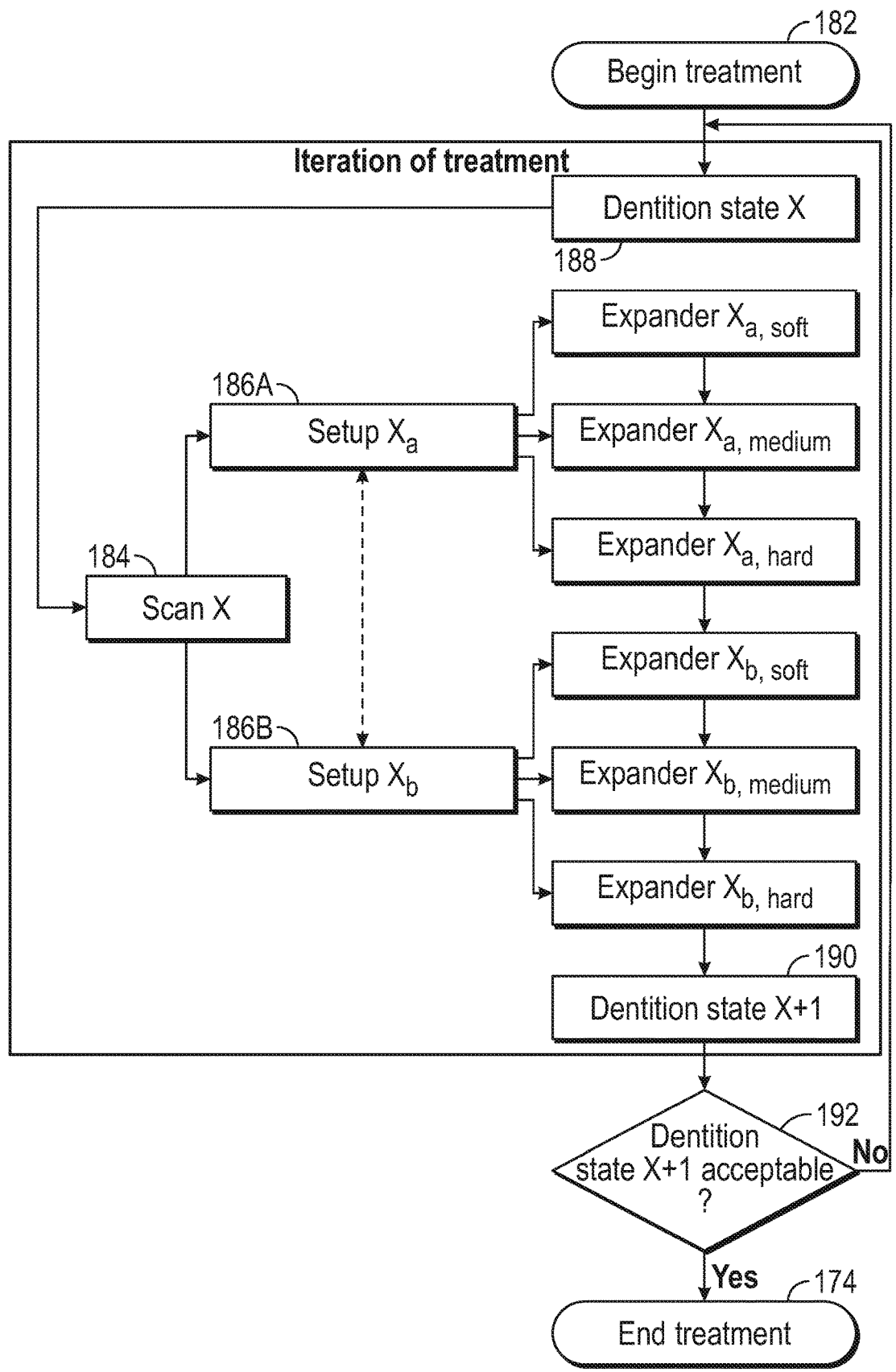
FIG. 9 is a flow diagram illustrating successive iterations of treatment using an ordered set of orthodontic palatal expanders.

FIG. 9 is a flow diagram illustrating successive iterations of treatment using an ordered set of orthodontic palatal expanders 72. The ordered set of orthodontic palatal expanders 72 is configured to reposition one or more teeth of a patient. In some examples, the ordered set of orthodontic palatal expanders 72 may include at least one of orthodontic palatal expanders 10, 30, and 40.

Treatment begins with the first iteration of treatment (182). At the beginning of the first iteration of treatment, the teeth of patient 62 are at their initial positions as represented by dentition state X (188). A scan of the teeth of patient 62, for example, as described above with respect to FIG. 4, is taken to facilitate the design of the ordered set of orthodontic palatal expanders 72 (184). From the scan of teeth and palate of patient 62, a computer, e.g., computing device 100, determines two different shapes and dimensions for orthodontic palatal expanders 72 in the ordered set: first setup $X_a$ 186A and second setup $X_b$ 188B. Example techniques for creating a digital model of teeth of patient 62 are described in U.S. Pat. No. 8,738,165 to Cinader, et al., titled, "METHODS OF PREPARING A VIRTUAL DENTITION MODEL AND FABRICATING A DENTAL RETAINER THEREFROM," and issued on May 27, 2014. U.S. Pat. No. 8,738, 165 is herein incorporated by reference in its entirety. The computer may determine first setup $X_a$ 186A and second setup $X_b$ 188B by first adjusting the digital model of the teeth of patient 62 to create a model of the desired position of the teeth and palate of patient 62 following the therapy. Then, the computer may create the shape and dimensions for orthodontic palatal expanders 72 in the ordered set based on the time and forces required to move the teeth and palate of patient 62 from the initial positions to their desired positions. For example, the computer model may adjust the thicknesses, positions, shapes, and dimensions of the first and second shells, the at least one split beam, the optional connecting plate, and the optional alignment tray of orthodontic palatal expanders 72 in the ordered set to produce the forces required to move the teeth and palate of patient 62 from the initial positions to their desired positions. The modeled forces applied by orthodontic palatal expanders 72 in the ordered set may further be based on the incremental positional movements of the teeth of patient 62 during the treatment. In this manner, the computer may design each of the orthodontic palatal expanders 72 in the ordered set according to expected forces applied on the teeth in the predicted positions of the teeth at the time during the treatment the orthodontic palatal expanders 72 in the ordered set is to be worn by patient 62.

In some examples, at least one, such as three, different orthodontic palatal expanders 72 in the set of orthodontic palatal expanders 72 can be manufactured using each of first setup $X_a$ 186A and second setup $X_b$ 188B to produce at least two, such as six, orthodontic palatal expanders 72 in the set of orthodontic palatal expanders 72. For example, first setup $X_a$ 186A may be used to manufacture first orthodontic palatal expander $X_{a,\ SOFT}$, second orthodontic palatal expander $X_{a,\ MED}$, and third orthodontic palatal expander $X_{a,\ HARD}$; and second setup $X_b$ 188B may be used to manufacture fourth orthodontic palatal expander $X_{b,\ SOFT}$, fifth orthodontic palatal expander $X_{b,\ MED}$, and sixth orthodontic palatal expander $X_{b,\ HARD}$. The first, second, and third orthodontic palatal expanders from first setup $X_a$ 186A may be substantially the same shape and dimensions, but may be formed from materials with different stiffness characteristics. For example, the second and third orthodontic palatal expanders from first setup $X_a$ 186A may have higher stiffness characteristics than the first orthodontic palatal expander from first setup $X_a$ 186A, and the third orthodontic palatal expander from first setup $X_a$ 186A may have higher stiffness characteristics than the second orthodontic palatal expander from first setup $X_a$ 186A. Similarly, the fourth, fifth, and sixth orthodontic palatal expanders may be substantially the same shape and dimensions, but comprise materials with different stiffness characteristics. In some examples, the first orthodontic palatal expander may have the same stiffness characteristics as the fourth orthodontic palatal expander, such as a relatively soft polymeric material. Similarly, the second orthodontic palatal expander may have the same stiffness characteristics as the fifth orthodontic palatal expander, such as a relatively stiffer polymeric material than the first orthodontic palatal expander. Likewise, the third orthodontic palatal expander may have the same stiffness characteristics as the sixth orthodontic palatal expander, such as a relatively stiffer polymeric material than the second orthodontic palatal expander.

The orthodontic palatal expanders in the ordered set of orthodontic palatal expanders 72 may be worn in sequence over time by the patient. For example, each of the six orthodontic palatal expanders in the ordered set of orthodontic palatal expanders 72 may be worn between about 2 weeks and about 12 weeks, such as between about 3 weeks and about 10 weeks or between about 4 weeks and about 8 weeks. Following the treatment plan using the six orthodontic palatal expanders 72, the teeth and palate of patient 62 may be at their final positions for the first iteration of treatment as represented by dentition state X+1 (190).

Once teeth of patient 62 are at or near dentition state X+1, the patient may return to the clinician who may evaluate the result of the first iteration of treatment (192). If the first iteration of treatment has resulted in acceptable final positions of the teeth and palate of patient 62, then the treatment may be ended (194). However, if the first iteration of treatment did not result in acceptable final positions of the teeth and palate of patient 62, one or more additional iterations of treatment may be performed. To begin the next iteration of treatment, the clinician may take another scan of the teeth and palate of patient 62 to facilitate the design of a subsequent ordered set of removable dental appliances (184). In some examples, evaluation of the result of the first iteration of treatment may include taking another scan of the teeth and palate of patient 62, in which case beginning the next iteration of treatment may simply involve forwarding the digital model of the teeth and palate of patient 62 to a manufacturing facility so that another ordered set of orthodontic palatal expanders 72 may be manufactured for patient 62 based on the new positions of the teeth and palate of patient 62. In yet other examples, the newly acquired scan may be used to create one or more iterations of orthodontic palatal expanders 72 in the clinician's facility.

The technique of FIG. 9 represents one specific example, and a variety of modifications may be made to the techniques of FIG. 9 within the spirit of this disclosure. For example, an ordered set of orthodontic palatal expanders 72 may include more or less than six removable dental appliances. As another example, each orthodontic palatal expander in the ordered set of orthodontic palatal expanders 72 may have unique shapes and dimensions, and each orthodontic palatal expander in the ordered set of orthodontic palatal expanders 72 may be made of material having substantially the same or similar stiffness characteristics.

Various examples have been described. These and other examples are within the scope of the following claims.

What is claimed is:

1. An orthodontic palatal expander comprising:
   a first shell configured to receive at least one tooth of a first posterior segment of a dental arch of a patient;
   a second shell configured to receive at least one tooth of a second posterior segment of the dental arch, the second segment opposing the first segment;
   a connecting plate positioned between the first shell and the second shell;
   a first split beam connected to the first shell and the connecting plate; and a second split beam connected to the second shell and the connecting plate,
   wherein each split beam comprises a first component beam, a second component beam, and a region between the first component beam and the second component beam, wherein the first component beam and second component beam are closely arranged in a plane either substantially parallel or substantially perpendicular to the occlusal plane, and
   wherein both the first and second split beams are configured to store energy in response to deformation and exert forces on the shell.

2. The orthodontic palatal expander of claim 1, wherein the region is at least partially filled with a relatively lower modulus, elastomeric material having a lower modulus than a material of the corresponding first and second component beams.

3. The orthodontic palatal expander of claim 1, wherein the region is substantially fully open.

4. The orthodontic palatal expander of claim 1, wherein the region between the first component beam and the second component beam extends from the first shell to the second shell.

5. The orthodontic palatal expander of claim 1, wherein the first component beam, second component beam, and region between of each split beam are arranged along substantially parallel paths between the connecting plate and the shell.

6. The orthodontic palatal expander of claim 5, wherein the connecting plate is configured to be positioned adjacent to a palate of the patient, and wherein the region is between the first component beam and the second component beam in the palatal direction.

7. The orthodontic palatal expander of claim 5, wherein the connecting plate is configured to be positioned adjacent to an anterior segment of the dental arch of the patient, and wherein the region is between the first component beam and the second component beam in a labio-lingual direction.

8. The orthodontic palatal expander of claim 7, wherein the first component beam is connected to an anterior portion of the first shell, and wherein the second component beam is connected to a more posterior portion of the first shell.

9. The orthodontic palatal expander of claim 1, wherein lengths of the first component beam and the second component beam and attachment points of the first component beam and the second component beam to the first shell are selected to control an amount and a direction of rotation of the first shell as the first shell causes buccal movement of the at least one tooth of the first posterior segment.

10. A system comprising:
    an ordered set of orthodontic palatal expanders configured to expand a palate of a patient, each orthodontic palatal expander in the ordered set of orthodontic palatal expanders comprising:
       a first shell configured to receive at least one tooth of the first posterior segment of a dental arch;
       a second shell configured to receive at least one tooth of a second posterior segment of the dental arch;
       a connecting plate positioned between the first shell and the second shell;
       a first split beam connected between the first shell and the connecting plate; and
       a second split beam connected to the connecting plate and the second shell,
    wherein each split beam comprises a first component beam, a second component beam, and a region between the first beam and the second beam, wherein the first component beam and second component beam are closely arranged in a plane either substantially parallel or substantially perpendicular to the occlusal plane, and
    wherein both the first and second split beams are configured to store energy in response to deformation and exert forces on the shell.

11. The system of claim 10, wherein the region is at least partially filled with, elastomeric material having a lower modulus than a material of the first and second component beams.

12. The system of claim 10, wherein the region is substantially fully open.

13. The system of claim 10, wherein the first component beam, second component beam, and region between of each split beam are arranged along substantially parallel paths between the connecting plate and the shell.

14. The system of claim 13, wherein the first component beam, the second component beam, a lingual or vestibular surface of the first shell, and the portion of the connecting plate to which the first component beam and the second component beam are connected define a parallelogram, a trapezoid, or a quadrilateral to control rotation of the first and second posterior segments.

15. The system of claim 14, wherein the direction of rotation is opposite of a reaction torque predicted of the at least one tooth of the first posterior segment during buccal movement of the at least one tooth of the first posterior segment.

16. The system of claim 10, wherein, for each palatal expander:
    the first shell is configured to receive a plurality of posterior teeth of the first posterior segment of the dental arch;
    the second shell is configured to receive a plurality of posterior teeth of the second posterior segment of the dental arch;

and wherein each palatal expander comprises a third split beam connected to the first shell and the connecting plate, and
a fourth split beam connected to the connecting plate and the second shell,
and
each split beam of the third and fourth split beams comprises a first component beam, a second component beam, and a respective region between the first component beam and the second component beam in the palatal direction, wherein both the third and fourth split beams are configured to store energy in response to deformation and exert forces on the shells.

17. A method comprising:
receiving, by a computing device, a digital representation of a three-dimensional (3D) dental anatomy of a patient, the dental anatomy providing initial positions of one or more teeth of the patient;
determining, by the computing device, dimensions and shapes of an orthodontic palatal expander for the patient, wherein
the dimensions and shapes of the removable dental appliance are configured to reposition the one or more teeth of the patient from their initial positions to adjusted positions when the orthodontic palatal expander is worn by the patient, and
the dimensions and shapes of the orthodontic palatal expander comprise:
a position, dimension and shape of a first shell configured to receive at least one tooth of a first posterior segment of a dental arch;
a position, dimension, and shape of a second shell configured to receive at least one tooth of a second posterior segment of the dental arch;
a position, dimension, and shape of a connecting plate between the first shell and the second shell, and
a position, dimension, and shape of a first split beam connected to the first shell and the connecting plate,
a position, dimension and shape of a second split beam connected to the second shell and the connecting plate,
wherein each split beam comprises a first component beam, a second component beam and a region between the first component beam and the second component beam; and
transmitting, by the computing device, a digital representation of the orthodontic palatal expander to a computer-aided manufacturing system; and
manufacturing the orthodontic palatal expander according to the digital representation.

18. The method of claim 17, wherein the three-dimensional (3D) dental anatomy of the patient further includes at least a portion of tooth roots, gingiva, periodontal ligaments (PDL), alveolar bone, or cortical bone.

19. The method of claim 17, wherein determining, by the computing device, dimensions and shapes of the orthodontic palatal expander includes accepting input from a user, wherein the input influences at least one of the dimensions and shapes.

20. The method of claim 17, wherein determining, by the computing device, dimensions and shapes of the orthodontic palatal expander includes selecting, by the computing device, the dimensions and shapes of the orthodontic palatal expander according to a set of predefined design constraints, the set of predefined design constraints including one or more of a group consisting of:
a minimum and a maximum localized force applied to one or more of the first or second teeth or the split beams;
a minimum and a maximum rotational force applied to one or more of the first or second teeth or the split beams;
a minimum and a maximum translational force applied to one or more of the first or second teeth or the split beams;
a minimum and a maximum total force applied to one or more of the first or second teeth or the split beams; and
a maximum strain applied to the orthodontic palatal expander when worn by the patient.

* * * * *